United States Patent
Ohtomo

(10) Patent No.: US 10,636,539 B2
(45) Date of Patent: Apr. 28, 2020

(54) COMPOUND, COMPOUND FABRICATION METHOD, AND GRAPHENE NANORIBBON FABRICATION METHOD

(71) Applicant: FUJITSU LIMITED, Kawasaki-shi, Kanagawa (JP)

(72) Inventor: Manabu Ohtomo, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 0 days.

(21) Appl. No.: 15/988,705

(22) Filed: May 24, 2018

(65) Prior Publication Data

US 2018/0362703 A1 Dec. 20, 2018

(30) Foreign Application Priority Data

Jun. 16, 2017 (JP) ................. 2017-118618

(51) Int. Cl.
*H01B 1/04* (2006.01)
*C01B 32/184* (2017.01)
(Continued)

(52) U.S. Cl.
CPC ............. *H01B 1/04* (2013.01); *C01B 32/184* (2017.08); *C01B 32/186* (2017.08);
(Continued)

(58) Field of Classification Search
CPC .......... H01B 1/04; H01B 1/124; H01B 1/128; C08G 61/00; C08G 61/02; C08G 61/10;
(Continued)

(56) References Cited

U.S. PATENT DOCUMENTS

2014/0301935 A1* 10/2014 Ivanovici ............. C01B 32/184
 423/448
2015/0225244 A1* 8/2015 Hintermann .......... C01B 32/184
 423/448
(Continued)

FOREIGN PATENT DOCUMENTS

| JP | 2016-505524 A | 2/2016 |
| JP | 2016-090510 A | 5/2016 |
| WO | 2013/061258 A1 | 5/2013 |

OTHER PUBLICATIONS

Hammerschmidt et al. ("Dynamic Stereochemistry of Open Chain Oligophenyl Compounds," Chem. Ber., 113, pp. 1121-1124) (Year: 1980).*

(Continued)

*Primary Examiner* — Matthew R Diaz
(74) *Attorney, Agent, or Firm* — Kratz, Quintos & Hanson, LLP

(57) ABSTRACT

A compound represented by the following general formula (1) is used as a precursor of a graphene nanoribbon:

(Continued)

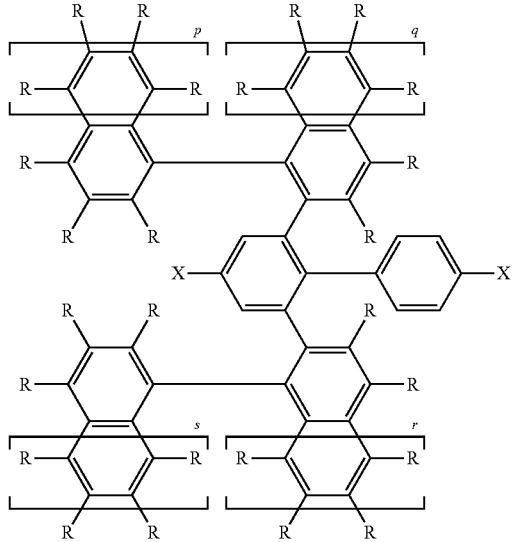
(1)
where X's are independent of each other and are leaving groups, R's are independent of one another and are hydrogen atoms, fluorine atoms, chlorine atoms, or 1-12C straight-chain, branched-chain, or cyclic alkyl groups, and each of p, q, r, and s is an integer in the range of 0 to 5.
4 Claims, 17 Drawing Sheets

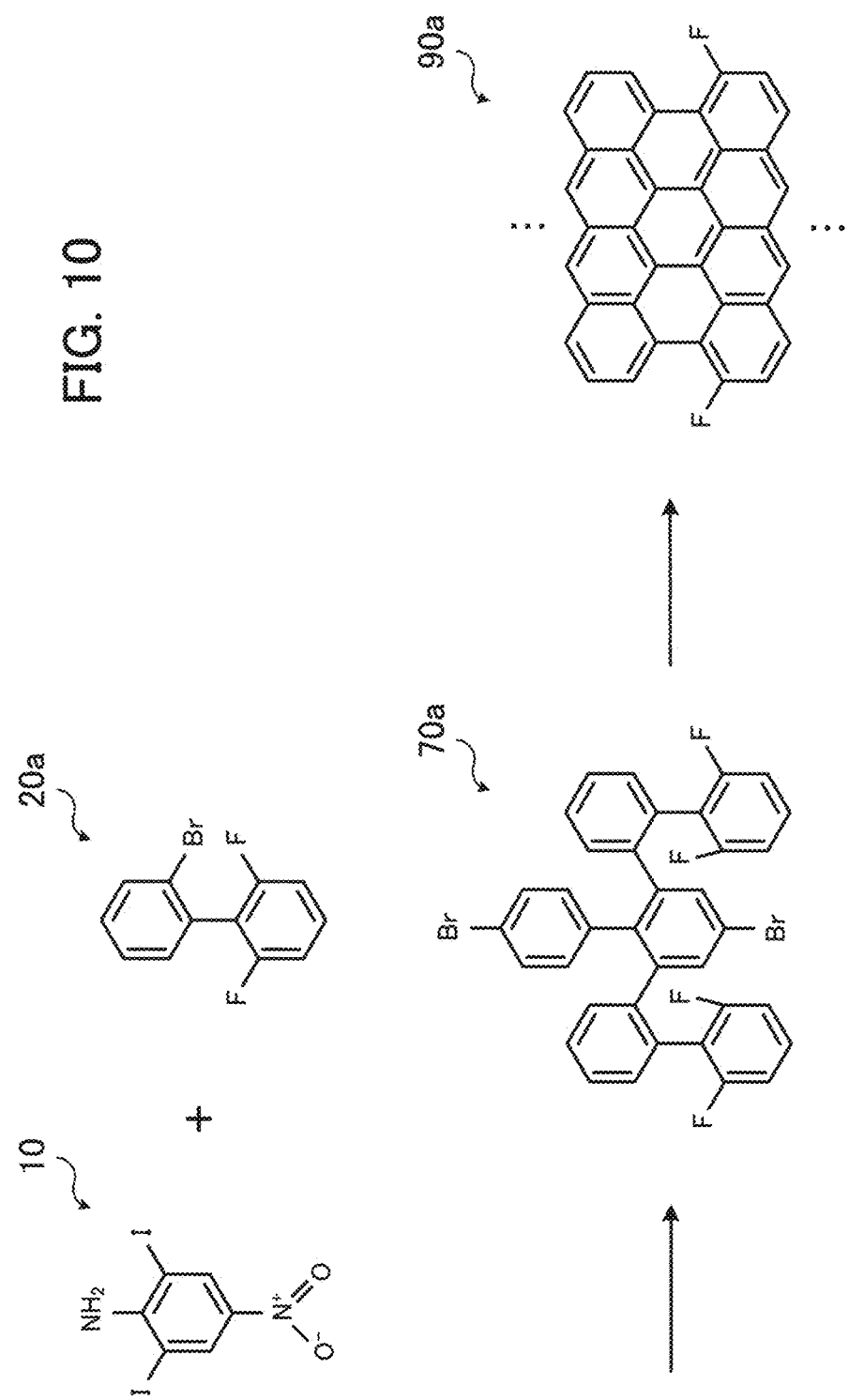

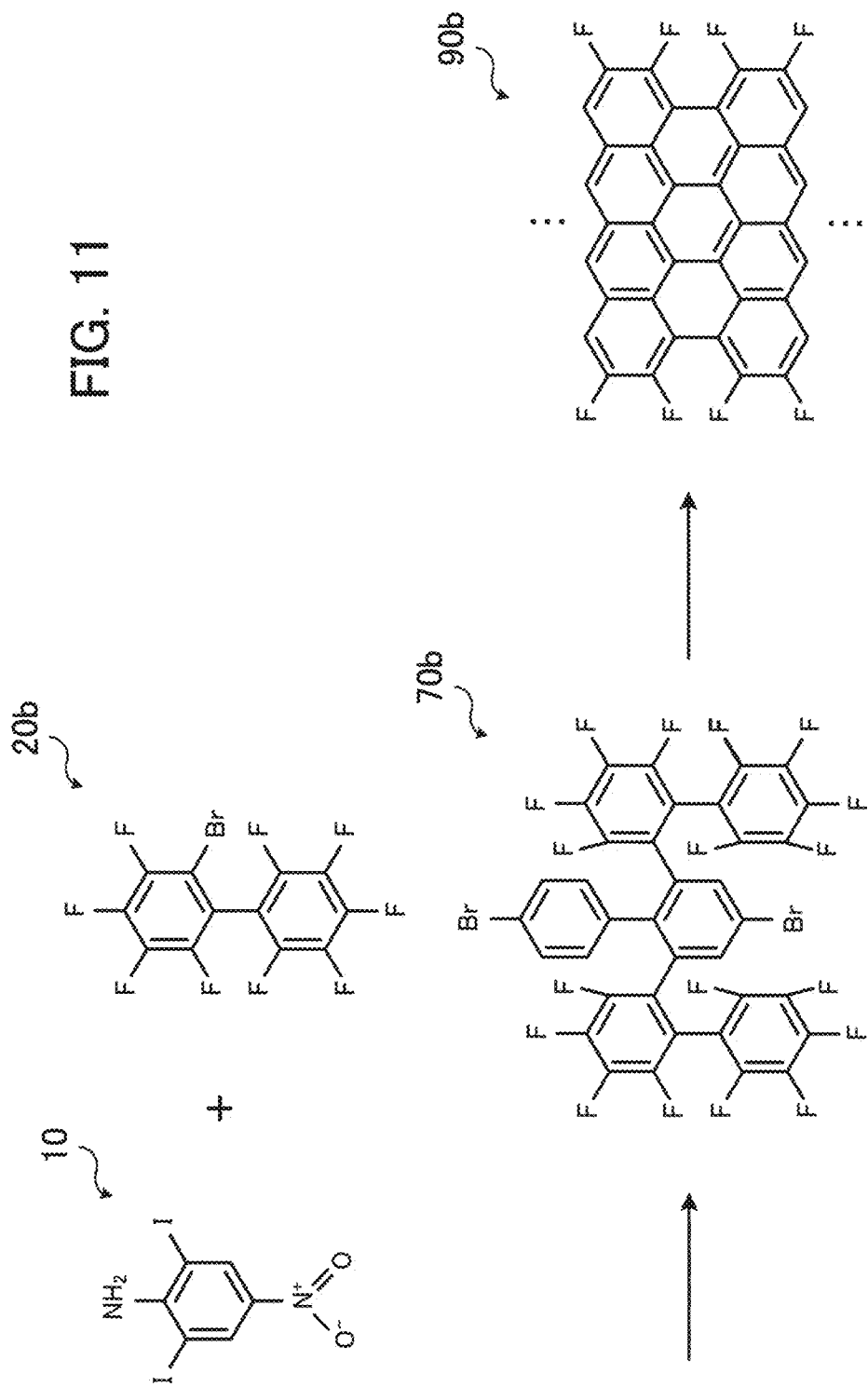

COMPOUND, COMPOUND FABRICATION METHOD, AND GRAPHENE NANORIBBON FABRICATION METHOD

CROSS-REFERENCE TO RELATED APPLICATION

This application is based upon, and claims the benefit of priority of, the prior Japanese Patent Application No. 2017-118618, filed on Jun. 16, 2017, the entire contents of which are incorporated herein by reference.

FIELD

The embodiments discussed herein are related to a compound, a compound fabrication method, and a graphene nanoribbon fabrication method.

BACKGROUND

A graphene nanoribbon is known as one of nanocarbon materials. In view of application of a graphene nanoribbon to a semiconductor device, its width and edge structure are controlled. By doing so, an attempt to obtain a semiconducting graphene nanoribbon having a band gap is made. An armchair edge is known as one of edge structures of graphene nanoribbons. Furthermore, a bottom-up method (bottom-up synthesis) is known as one of methods for obtaining a graphene nanoribbon. With this bottom-up method a graphene nanoribbon is synthesized by polymerizing precursor compounds.

International Publication Pamphlet No. WO2013/061258

Jinming Cai, Pascal Ruffieux, Rached Jaafar, Marco Bieri, Thomas Braun, Stephan Blankenburg, Matthias Muoth, Ari P. Seitsonen, Moussa Saleh, Xinliang Feng, Klaus Mullen & Roman Fasel, "Atomically precise bottom-up fabrication of graphene nanoribbons" Nature, Vol. 466, pp. 470-473, 2010

With conventional compounds known as a precursor of a graphene nanoribbon, there are cases where a graphene nanoribbon having a band gap, that is to say, width suitable for semiconductor devices is not synthesized from the viewpoint of structure. In addition, control exercised in the process for synthesizing a graphene nanoribbon may be difficult from the viewpoint of the structure of a compound used as a precursor. As a result, there are cases where a graphene nanoribbon suitable for semiconductor devices is not synthesized.

SUMMARY

According to an aspect, there is provided a compound represented by the following general formula (1):

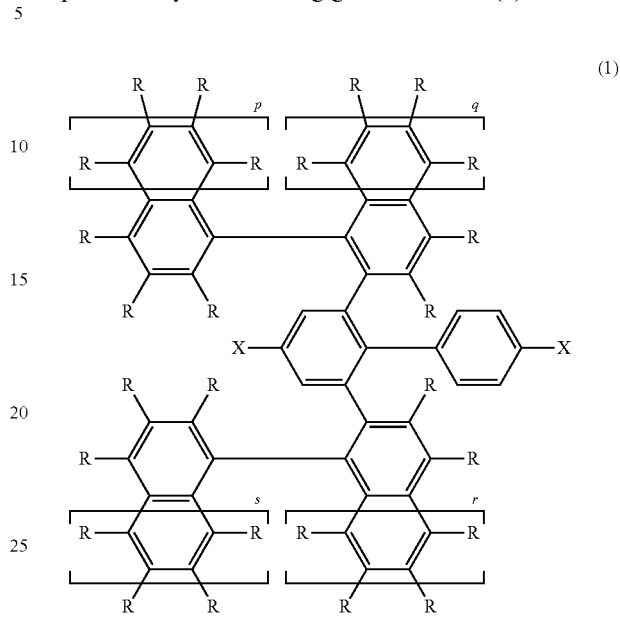

(1)

wherein X's are independent of each other and are leaving groups, R's are independent of one another and are hydrogen atoms, fluorine atoms, chlorine atoms, or 1-12C straight-chain, branched-chain, or cyclic alkyl groups, and each of p, q, r, and s is an integer in the range of 0 to 5.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 10 is a view for describing another example of a route of the synthesis of a precursor and a graphene nanoribbon (part 1);

FIG. 11 is a view for describing another example of a route of the synthesis of a precursor and a graphene nanoribbon (part 2);

DESCRIPTION OF EMBODIMENTS

Two examples in which a graphene nanoribbon is obtained by the bottom-up synthesis will be described first with reference to FIG. 1 and FIG. 2.

Figure 1:
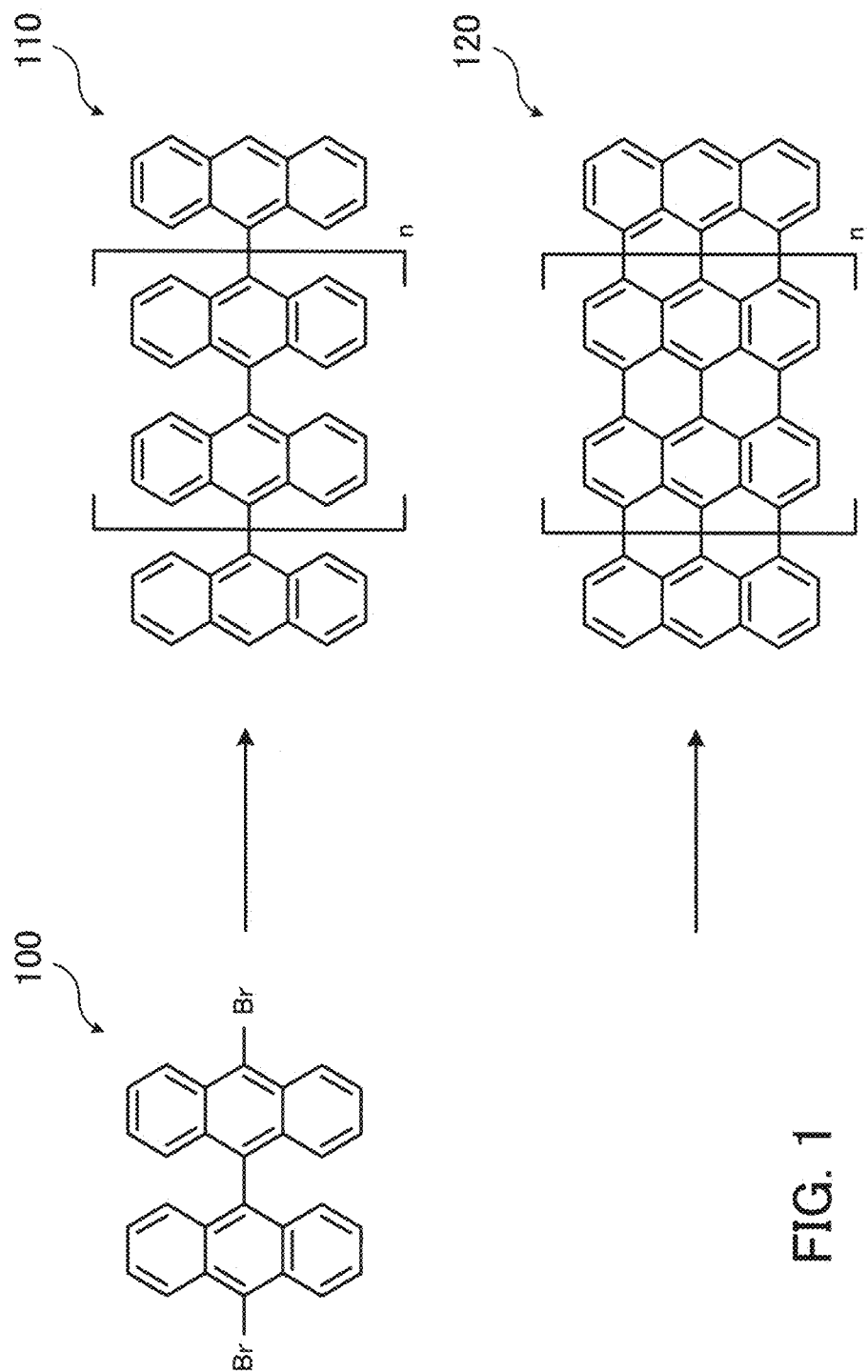
FIG. 1 is a view for describing a first example of the synthesis of a graphene nanoribbon.

FIG. 1 is a view for describing a first example of the synthesis of a graphene nanoribbon. FIG. 2 is a view for describing a second example of the synthesis of a graphene nano ribbon.

In the first example illustrated in FIG. 1, a graphene nanoribbon (7ACGNR) 120 having an armchair edge and having width corresponding to seven carbon atoms is synthesized with 10,10'-dibromo-9,9'-bianthryl (DBBA) 100 as a precursor. The DBBA 100, which is a precursor, is deposited over a catalytic metal substrate and is polymerized (Ullmann reaction). By doing so, a polymer chain 110 is obtained. The 7ACGNR 120 is obtained by aromatization (aromatic cyclization) of the polymer chain 110 by a dehydrogenation reaction. n in the polymer chain 110 or the 7ACGNR 120 illustrated in FIG. 1 indicates a polymerization degree.

Figure 2:
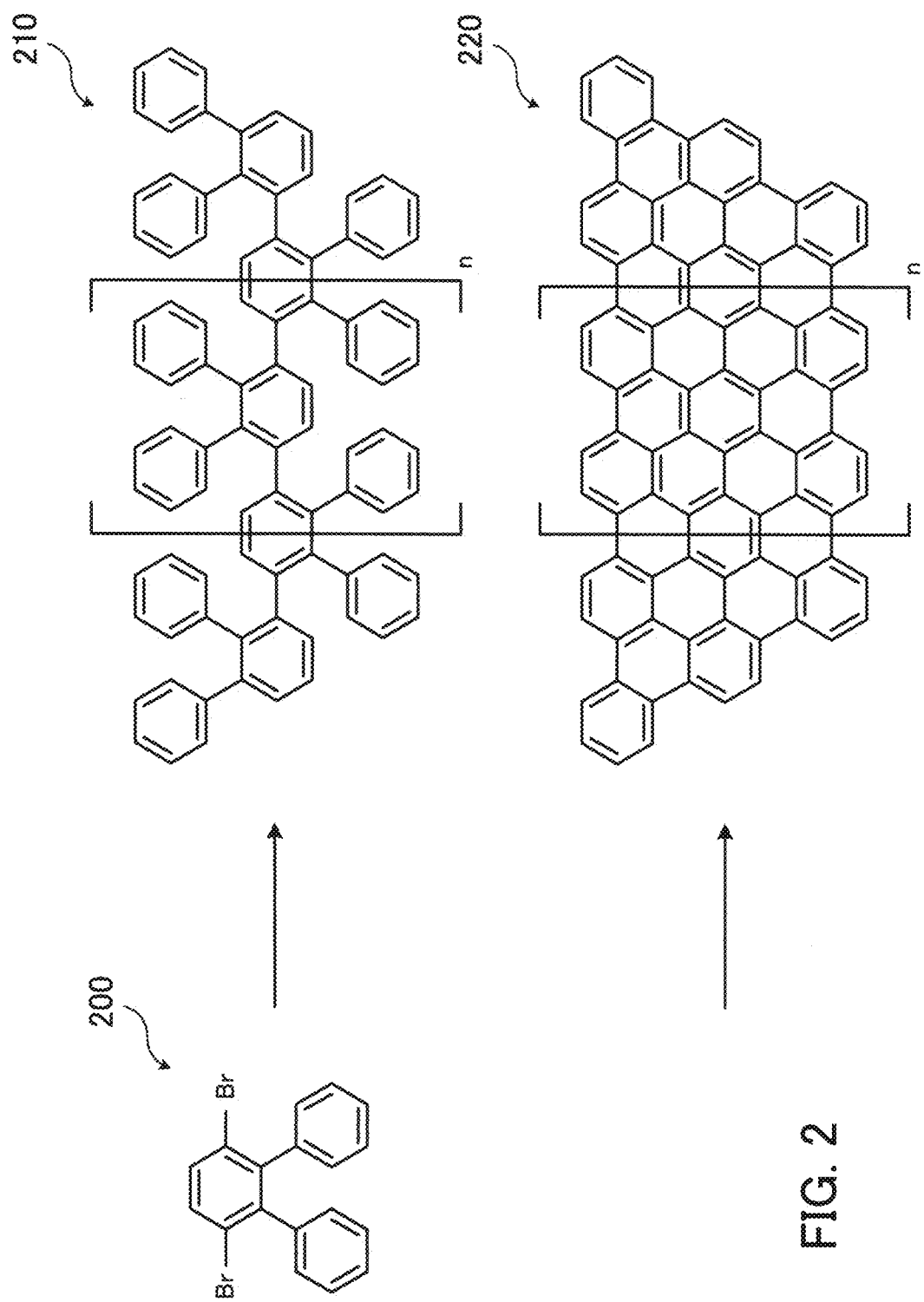
FIG. 2 is a view for describing a second example of the synthesis of a graphene nanoribbon.

In the second example illustrated in FIG. 2, a graphene nanoribbon (9ACGNR) 220 having an armchair edge and having width corresponding to nine carbon atoms is synthesized with 3',6'-dibromo-1,1':2',1''-terphenyl (DBTP) 200 as a precursor. The DBTP 200, which is a precursor, is deposited over a catalytic metal substrate and is polymerized (Ullmann reaction). By doing so, a polymer chain 210 is obtained. The 9ACGNR 220 is obtained by aromatic cyclization of the polymer chain 210 by a dehydrogenation reaction. n in the polymer chain 210 or the 9ACGNR 220 illustrated in FIG. 2 indicates a polymerization degree.

Usually the width of a graphene nanoribbon has an influence on its band gap. There is a tendency for the band gap of a graphene nanoribbon to become smaller with an increase in its width. The width of a graphene nanoribbon is controlled by the structure of a compound used as a precursor of the graphene nanoribbon such as the DBBA 100 in the first example or the DBTP 200 in the second example.

The following problems arise in the synthesis of a graphene nanoribbon illustrated in FIG. 1 or FIG. 2.

With the first example illustrated in FIG. 1, the 7ACGNR 120 obtained has a comparatively large band gap. If the 7ACGNR 120 is applied to a semiconductor device, it is not always easy to realize good electrode bonding. Alternatively, the types of usable electrode materials are limited.

With the second example illustrated in FIG. 2, on the other hand, the 9ACGNR 220 obtained has a comparatively small band gap. However, the molecular weight of the DBTP 200, which is a precursor, is small and its sublimation temperature is low. Therefore, it is difficult to control a deposition rate. The DBTP 200 does not adhere to an ordinary crystal oscillator film thickness meter at room temperature. Accordingly, it is also difficult to estimate a deposition amount.

In addition, the first example and the second example have a common problem. It is not always easy to control the orientation of the 7ACGNR 120 or the 9ACGNR 220 or to control the orientation of the polymer chain 110 or the polymer chain 210 which are an intermediate of the 7ACGNR 120 or the 9ACGNR 220.

A graphene nanoribbon is a one-dimensional material. If a graphene nanoribbon is applied to a semiconductor device, it is important to control the orientation of the graphene nanoribbon relative to an electrode. For example, it is assumed that a field-effect transistor (FET) in which a source electrode and a drain electrode are connected by a graphene nanoribbon is formed. If a graphene nanoribbon grows in a random orientation state, it is difficult to fabricate FETs having stable characteristics with a high yield. If a specific catalytic metal substrate, such as a single crystal metal substrate having a high index plane, is used for the synthesis of a graphene nanoribbon, it is possible to control the orientation of the graphene nanoribbon. However, this may lead to a significant increase in the costs.

In view of the above problems, a method in which the following compound is used as a precursor and in which a graphene nanoribbon is obtained by the bottom-up synthesis will be described as a first embodiment.

First a compound used as a precursor of a graphene nanoribbon will be described.

A compound used as a precursor of a graphene nanoribbon has a structure represented by the following formula (2):

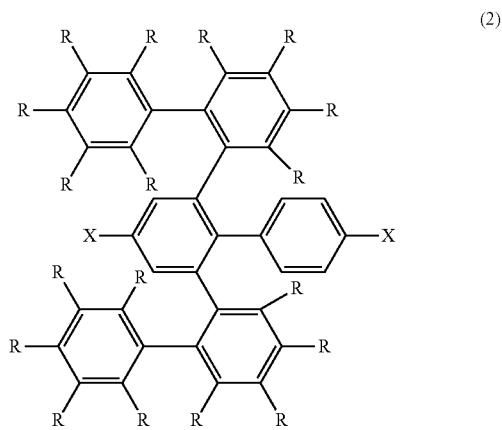

(2)

where X's are independent of each other, are leaving groups, and are preferably bromine (Br) atoms, chlorine (Cl) atoms, or iodine (I) atoms and R's are independent of one another and are hydrogen (H) atoms, fluorine (F) atoms, chlorine (Cl) atoms, or 1-12C straight-chain, branched-chain, or cyclic alkyl groups.

The precursor represented by formula (2) is synthesized in the following way.

First a compound represented by the following formula (3) and a compound represented by the following formula (4) are prepared. In the formula (3),

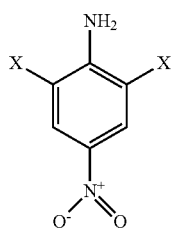

(3)

X's are independent of each other, are leaving groups, and are, for example, I atoms or Br atoms. In the formula (4),

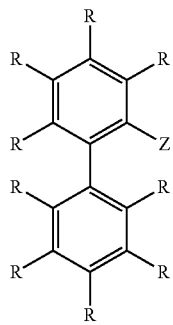

(4)

R's are independent of one another and are H atoms, F atoms, Cl atoms, or 1-12C straight-chain, branched-chain, or cyclic alkyl groups and Z is a boronyl group ($B(OH)_2$ group), a Br atom, or an I atom.

Coupling between the compound represented by formula (3) and the compound represented by formula (4) is performed by a Suzuki coupling or an Ullmann reaction to obtain a compound represented by the following formula (5):

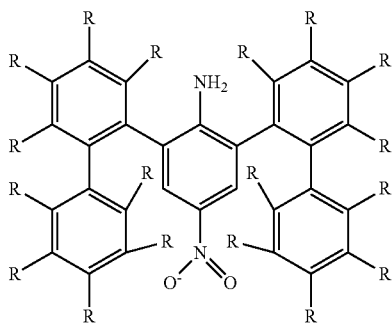

(5)

where R's are independent of one another and are H atoms, F atoms, Cl atoms, or 1-12C straight-chain, branched-chain, or cyclic alkyl groups.

An amino group ($NH_2$ group) of the obtained compound represented by formula (5) is converted to a leaving group to obtain a compound represented by the following formula (6):

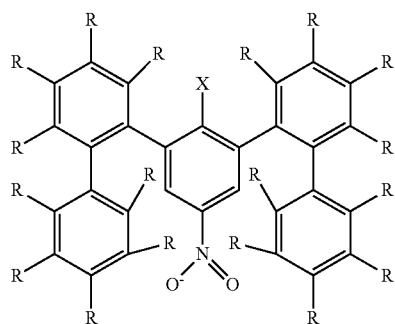

(6)

where R's are independent of one another and are H atoms, F atoms, Cl atoms, or 1-12C straight-chain, branched-chain, or cyclic alkyl groups and X is a leaving group such as an I atom. For example, the $NH_2$ group of the compound represented by formula (5) is converted to an I atom by a Sandmeyer reaction or the like.

Coupling between the obtained compound represented by formula (6) and a compound represented by the following formula (7) is performed by a Suzuki coupling or an Ullmann reaction to obtain a compound represented by the following formula (8). In the formula (7),

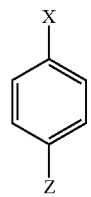

(7)

X is a leaving group such as a Br atom and Z is a $B(OH)_2$ group, a Br atom, or an I atom. In the formula (8),

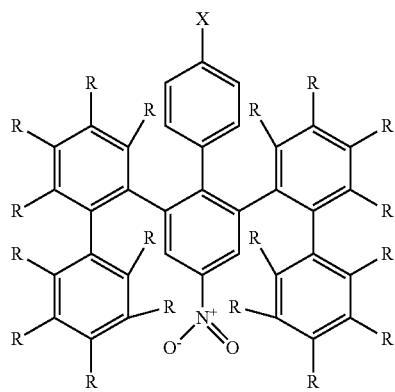

(8)

X is a leaving group such as a Br atom and R's are independent of one another and are H atoms, F atoms, Cl atoms, or 1-12C straight-chain, branched-chain, or cyclic alkyl groups.

A nitro group ($NO_2$ group) of the obtained compound represented by formula (8) is converted to a leaving group X to obtain a compound represented by the following formula (9):

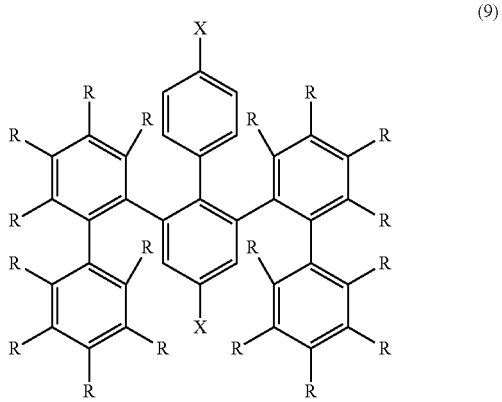

(9)

X is a leaving group such as a Br atom and R's are independent of one another and are H atoms, F atoms, Cl atoms, or 1-12C straight-chain, branched-chain, or cyclic alkyl groups. For example, an $NO_2$ group of the compound represented by formula (8) is reduced to an $NH_2$ group and the $NH_2$ group is converted to a leaving group such as a Br atom.

The compound represented by formula (9) is used as a precursor of a graphene nanoribbon.

Figure 3:
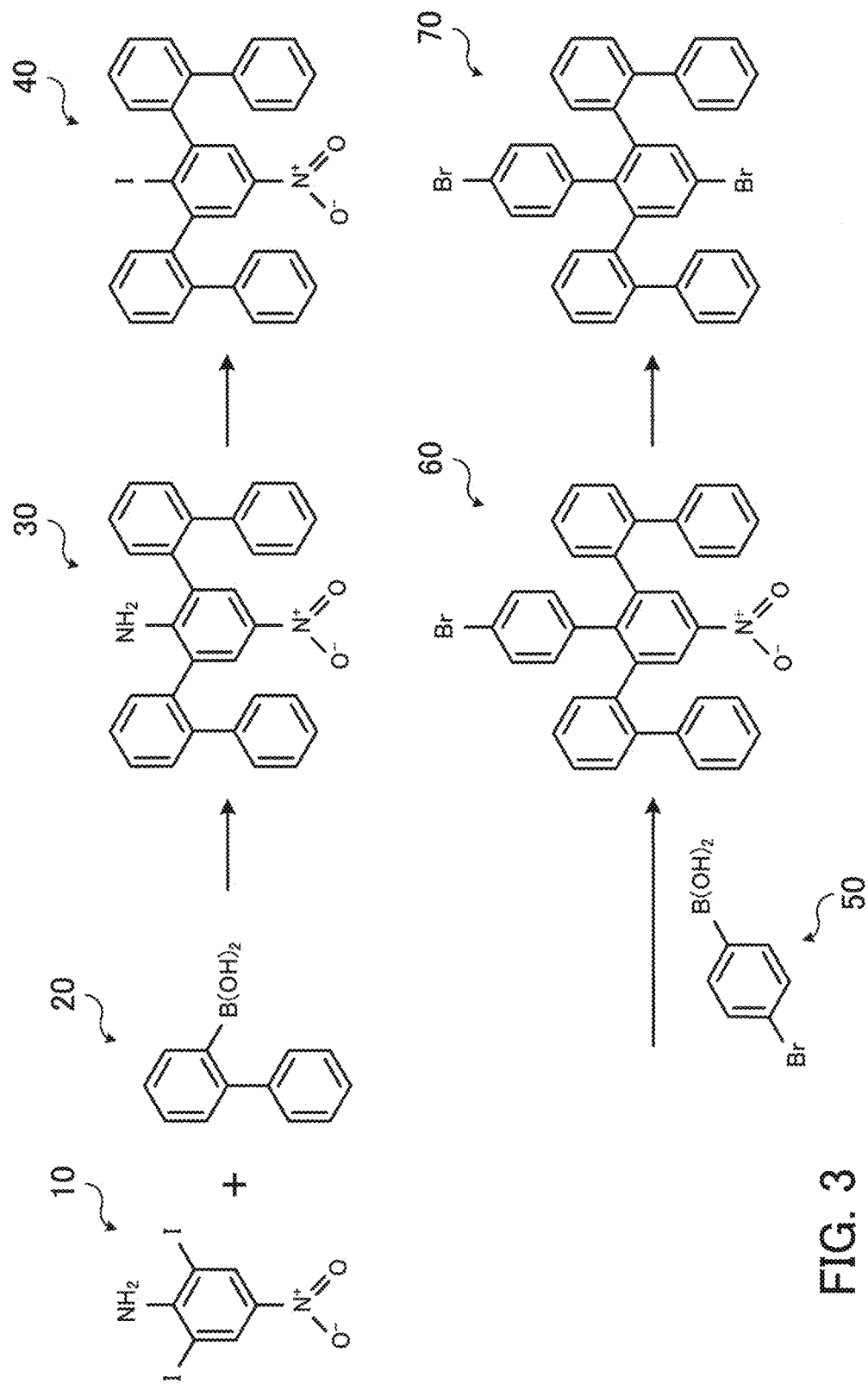
FIG. 3 illustrates an example of a route of the synthesis of a precursor.

An example of the synthesis of the above precursor of a graphene nanoribbon is illustrated in FIG. 3.

The obtained compound 30 is iodized to convert the $NH_2$ group to an I atom. By doing so, a compound 40 corresponding to formula (6) (X and R's in formula (6) are an I atom and H atoms respectively) is obtained.

Furthermore, coupling between the compound 40 obtained in this way and a compound 50 corresponding to formula (7) (X and Z in formula (7) are a Br atom and a $B(OH)_2$ group respectively) is performed by a Suzuki coupling to obtain a compound 60 corresponding to formula (8) (X and R's in formula (8) are a Br atom and H atoms respectively).

An $NO_2$ group of the obtained compound 60 is reduced to an $NH_2$ group and the $NH_2$ group is converted to a Br atom by bromization. By doing so, a compound corresponding to formula (9) (X's and R's in formula (9) are Br atoms and H atoms respectively), that is to say, 4'''''-5''-dibromo-1,1':2', 1'':2'',1'''':3''',1''':2''',1''''-sexiphenyl (DBSP) 70 is obtained.

For example, the DBSP 70 obtained in this way is used as a precursor of a graphene nanoribbon.

The synthesis of a graphene nanoribbon performed by the use of the above precursor will now be described.

In order to synthesize a graphene nanoribbon, first a precursor represented by formula (2) or formula (9) is deposited over a heated catalytic metal substrate in a vacuum (vacuum deposition). When this vacuum deposition is performed, a plurality of precursors deposited over the catalytic metal substrate are polymerized to synthesize a polymer chain of an aromatic compound represented by the following formula (10):

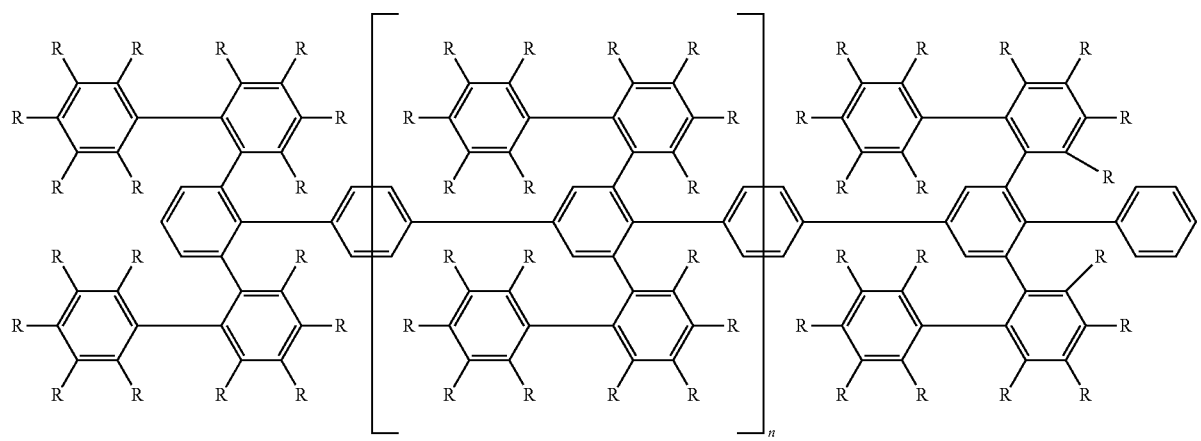

(10)

FIG. 3 illustrates an example of a route of the synthesis of the precursor.

In the example of FIG. 3, 2,6-diiodo-4-nitroaniline is used as a compound 10 corresponding to formula (3) and 2-biphenyl-boronic acid is used as a compound 20 corresponding to formula (4). The compound 10 has a structure corresponding to formula (3) in which X's are I atoms. The compound 20 has a structure corresponding to formula (4) in which R's are H atoms and in which Z is a $B(OH)_2$ group.

Coupling between the compound 10 and the compound 20 is performed by a Suzuki coupling with the compound 10 and the compound 20 as starting materials to obtain a compound 30 corresponding to formula (5) (R's in formula (5) are H atoms).

where R's are independent of one another and are H atoms, F atoms, Cl atoms, or 1-12C straight-chain, branched-chain, or cyclic alkyl groups and n indicates a polymerization degree and is an integer in the range of 0 to 100000.

The formed polymer chain is heated further in a vacuum at a higher temperature (high temperature heating). When this high temperature heating is performed, aromatic cyclization progresses in the polymer chain over the catalytic metal substrate. As a result, a graphene nanoribbon (9ACGNR) represented by the following formula (11) is synthesized. This graphene nanoribbon has an armchair edge and has width corresponding to nine carbon atoms. In the formula (11),

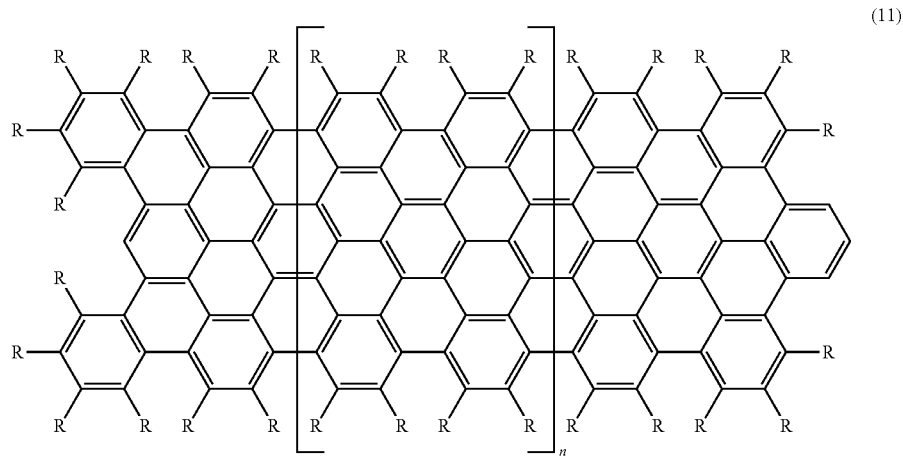

(11)

R's are independent of one another and are H atoms, F atoms, Cl atoms, or 1-12C straight-chain, branched-chain, or cyclic alkyl groups and n indicates a polymerization degree and is an integer in the range of 0 to 100000.

Figure 4:
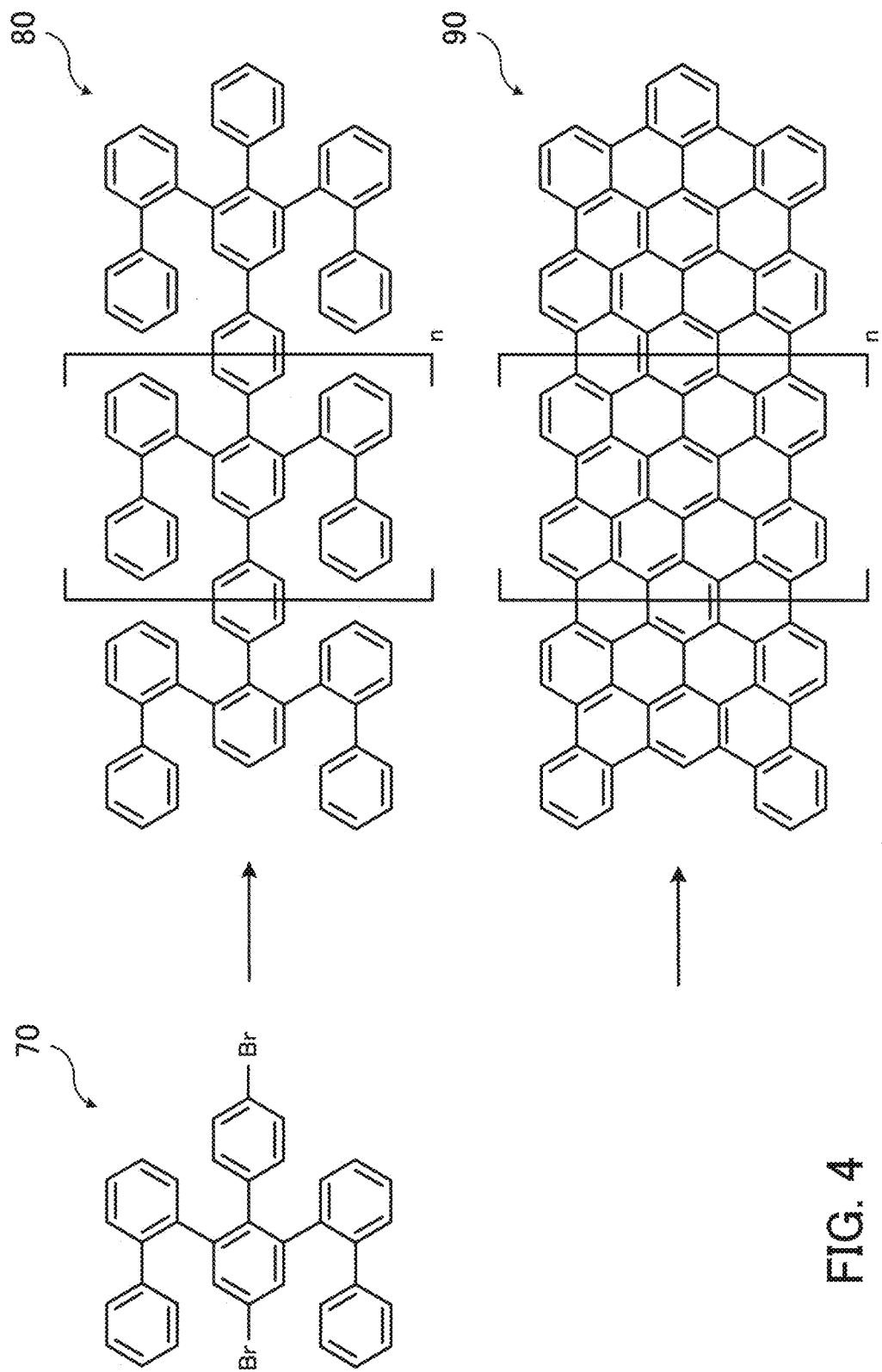
FIG. 4 illustrates an example of a route of the synthesis of a graphene nanoribbon.

An example of the synthesis of the above graphene nanoribbon is illustrated in FIG. 4.

FIG. 4 illustrates an example of a route of the synthesis of the graphene nanoribbon.

In the example of FIG. 4, the DBSP 70 (FIG. 3) is used as a precursor of the graphene nanoribbon. The synthesis is performed in the following way by the use of the DBSP 70. First the DBSP 70 is vacuum-deposited over a heated catalytic metal substrate. A (111) plane, a (110) plane, a (100) plane, or a high index plane, such as a (788) plane, of gold (Au), silver (Ag), copper (Cu), or the like is used as the catalytic metal substrate. Description will now be given with an Au (111) plane as an example. The Au (111) plane purified in an ultrahigh vacuum is kept at a temperature of about 200 to 300° C. and the DBSP 70 is vacuum-deposited thereover. At this time it is desirable to control a deposition amount so that about one-molecule layer will be formed. A plurality of DBSPs 70 deposited are polymerized over the Au (111) plane by an Ullmann reaction. As a result, a polymer chain 80 illustrated in FIG. 4 is synthesized.

After the above vacuum deposition, the Au (111) plane over which the polymer chain 80 is formed is heated in a vacuum at a higher temperature of about 350 to 450° C. This high temperature heating causes a dehydrogenation reaction or the like in the polymer chain 80 over the Au (111) plane and aromatic cyclization progresses. As a result, a graphene nanoribbon illustrated in FIG. 4, that is to say, a 9ACGNR 90 is synthesized.

An effect obtained by using a compound represented by formula (2) as a precursor of a graphene nanoribbon will now be described.

The DBSP 70 illustrated in FIG. 3 and FIG. 4 and the polymer chain 80 and the 9ACGNR 90 of FIG. 4 synthesized by the use of the DBSP 70 are taken as an example. Furthermore, the DBBA 100 illustrated in FIG. 1 and the polymer chain 110 and the 7ACGNR 120 of FIG. 1 synthesized by the use of the DBBA 100 and the DBTP 200 illustrated in FIG. 2 and the polymer chain 210 and the 9ACGNR 220 of FIG. 2 synthesized by the use of the DBTP 200 are used for comparison.

First the band gap of the 9ACGNR 90 synthesized by the use of the DBSP 70 is smaller than that of the 7ACGNR 120 synthesized by the use of the DBBA 100. The width of the 7ACGNR 120 is smaller than that of the 9ACGNR 90.

FIGS. 5A and 5B and FIGS. 6A and 6B are views for describing the band structures of the graphene nanoribbons.

Figure 5A:
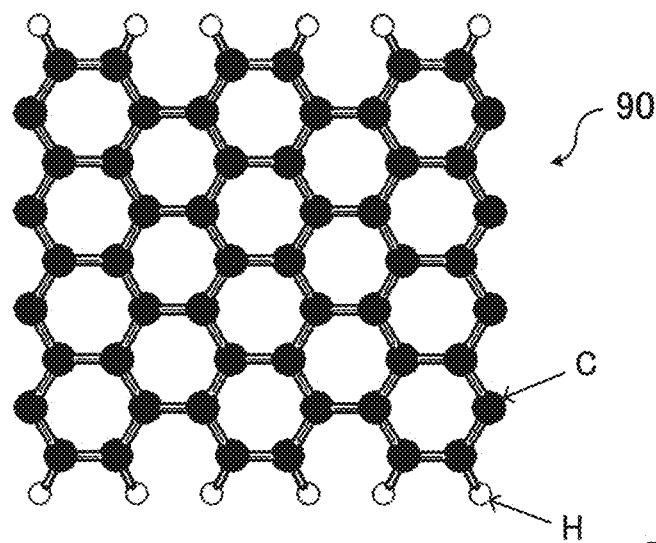
FIGS. 5A and 5B are views for describing the band structure of a graphene nanoribbon (part 1)
Figure 5B:
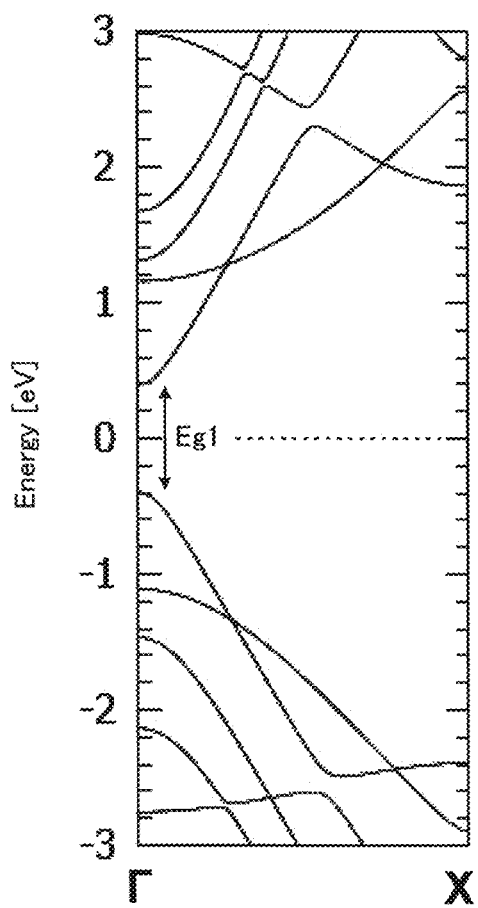

FIG. 5A illustrates the 9ACGNR 90 synthesized by the use of the DBSP 70. FIG. 5B illustrates a result obtained by estimating its band structure by a density functional method. For comparison, FIG. 6A illustrates the 7ACGNR 120 synthesized by the use of the DBBA 100 and FIG. 6B illustrates a result obtained by estimating its band structure by the density functional method.

Figure 6A:
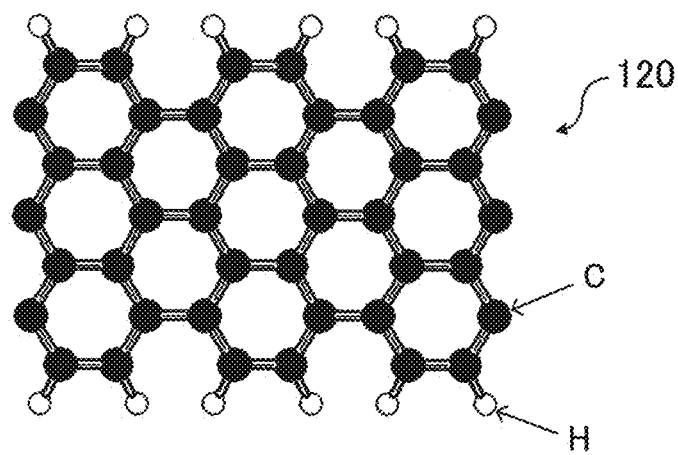
FIGS. 6A and 6B are views for describing the band structure of a graphene nanoribbon (part 2)
Figure 6B:
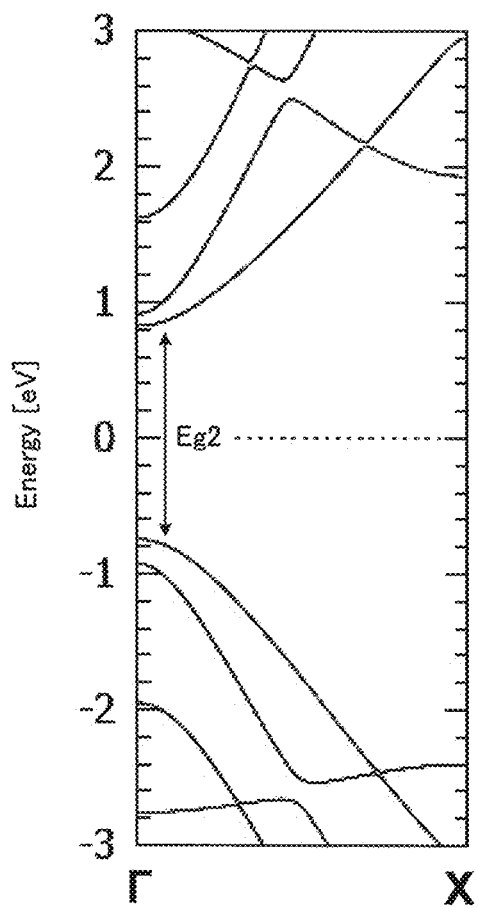

In FIGS. 6A and 6B, a band gap Eg2 of the 7ACGNR 120 is estimated to be 1.56 eV. This value is smaller than a value experimentally reported. This is a known problem as the limit of the density functional method in the case of estimating a band gap of a graphene nanoribbon. However, it is possible to correctly estimate a relative magnitude relationship. In FIGS. 5A and 5B, a band gap Eg1 of the 9ACGNR 90 is estimated by the density functional method to be 0.79 eV. The band gap Eg1 of the 9ACGNR 90 is about half of the band gap Eg2 of the 7ACGNR 120.

As has been described, a small band gap is realized by the 9ACGNR 90 synthesized by the use of the DBSP 70, compared with the 7ACGNR 120 synthesized by the use of the DBBA 100.

In addition, the molecular weight of the DBSP 70 used for the synthesis of the 9ACGNR 90 is 616. On the other hand, the molecular weight of the DBBA 100 (FIG. 1) used for the synthesis of the 7ACGNR 120 is 512 and the molecular weight of the DBTP 200 (FIG. 2) used for the synthesis of the 9ACGNR 220 is 388. The molecular weight (=616) of the DBSP 70 is sufficiently heavier than the molecular weight (=388) of the DBTP 200 and is heavier than the molecular weight (=512) of the DBBA 100. Accordingly, the sublimation temperature of the DBSP 70 is higher than that of the DBTP 200 and is higher than that of the DBBA 100.

The sublimation temperature of the DBSP 70 is comparatively high. Therefore, it is easy to control a deposition rate at the time of synthesis using the DBSP 70 (at the time of depositing the DBSP 70 over a catalytic metal substrate), compared with a case where the DBTP 200 or the DBBA 100 is used.

Furthermore, improvement in orientation is expected by an interaction between molecules (polymer chains 80 or 9ACGNRs 90) synthesized by the use of the DBSP 70.

FIGS. 7A through 9B are views for describing an interaction between molecules synthesized from a precursor.

Figure 7A:
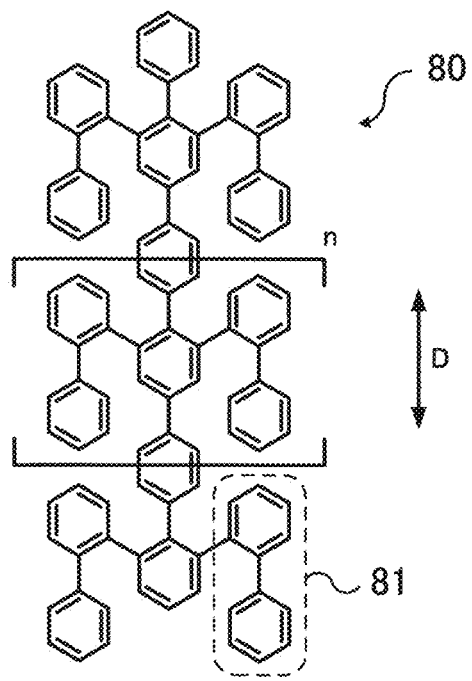
FIGS. 7A through 7C are views for describing an interaction between molecules synthesized from a precursor (part 1)
Figure 7B:
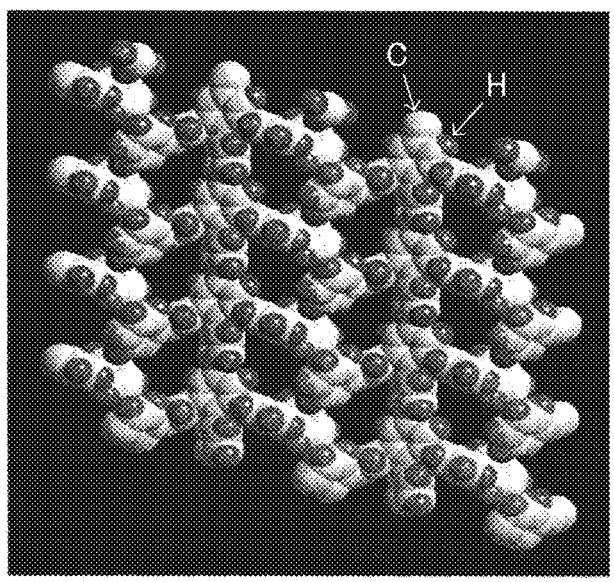
Figure 7C:
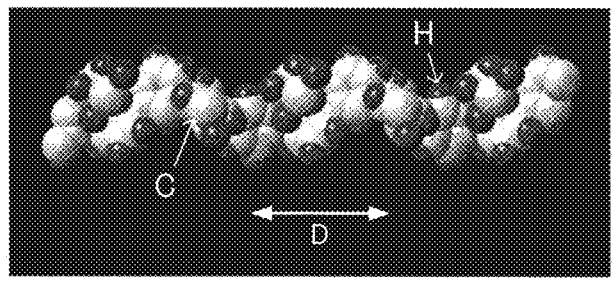
Figure 8A:
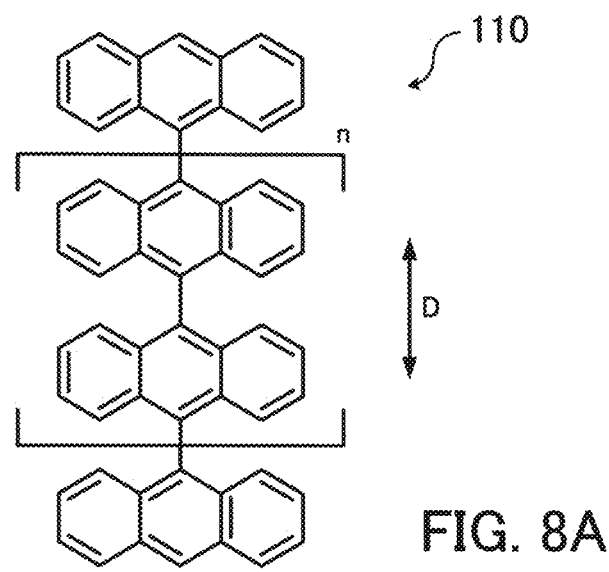
FIGS. 8A and 8B are views for describing an interaction between molecules synthesized from a precursor (part 2)
Figure 8B:
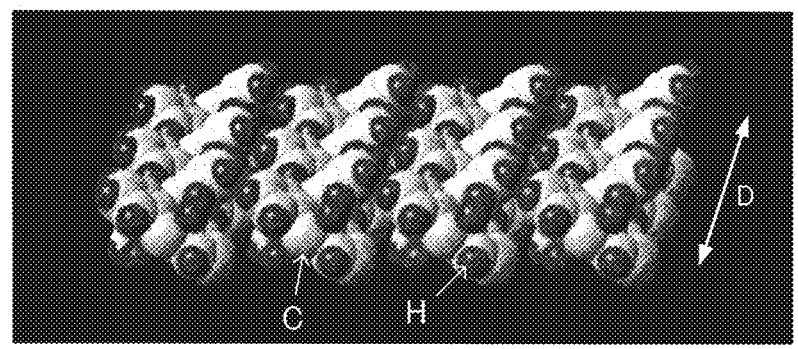
Figure 9A:
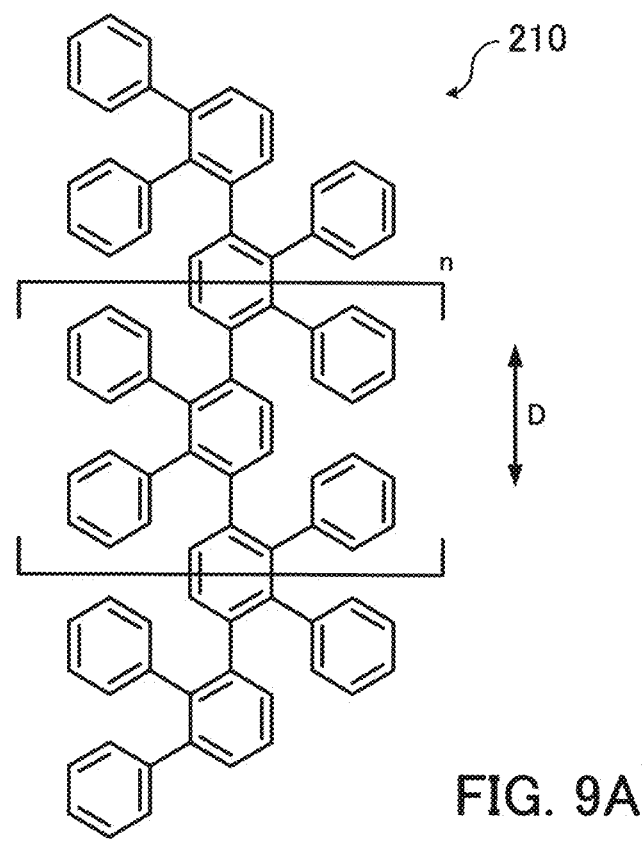
FIGS. 9A and 9B are views for describing an interaction between molecules synthesized from a precursor (part 3)
Figure 9B:
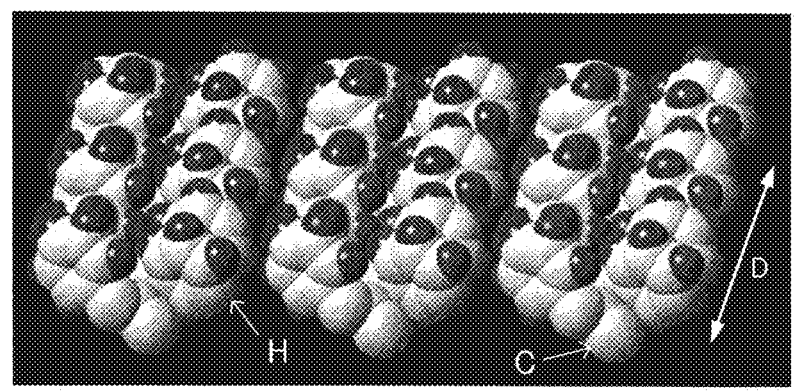

FIG. 7A illustrates the polymer chain 80 synthesized from the DBSP 70. FIG. 7B is a plan view of a plurality of polymer chains 80 two-dimensionally aggregated. FIG. 7C is a side view of a plurality of polymer chains 80 two-dimensionally aggregated. For comparison, FIG. 8A illustrates the polymer chain 110 synthesized from the DBBA 100. FIG. 8B is a perspective view of a plurality of polymer chains 110 two-dimensionally aggregated. FIG. 9A illustrates the polymer chain 210 synthesized from the DBTP 200. FIG. 9B is a perspective view of a plurality of polymer chains 210 two-dimensionally aggregated. n indicated in FIG. 7A, FIG. 8A, and FIG. 9A represents a polymerization degree. D indicated in FIGS. 7A through 7C, FIGS. 8A and 8B, and FIGS. 9A and 9B represents the extending direction of a polymer.

The polymer chain 80 illustrated in FIG. 7A and synthesized from the DBSP 70 is an aromatic compound in which a plurality of aromatic rings are linked, and contains $\pi$ electrons. Accordingly, a $\pi$-$\pi$ interaction acts between side chains 81 of adjacent polymer chain 80. As illustrated in FIG. 7B and FIG. 7C, polymer chains 80 synthesized from the DBSP 70 are two-dimensionally aggregated. Cohesive energy at that time is calculated. As a result, it turns out that a gain of an aggregate of the polymer chains 80 caused by the $\pi$-$\pi$ interaction is 17.9 meV compared with infinity.

Similarly, with the polymer chain 110 illustrated in FIG. 8A and synthesized from the DBBA 100 or the polymer chain 210 illustrated in FIG. 9A and synthesized from the DBTP 200, the $\pi$-$\pi$ interaction acts between adjacent polymer chains 110 or between adjacent polymer chains 210. As illustrated in FIG. 8B, polymer chains 110 synthesized from the DBBA 100 are two-dimensionally aggregated. Cohesive energy at that time is calculated. As a result, it turns out that a gain of an aggregate of the polymer chains 110 caused by the $\pi$-$\pi$ interaction is only 8.7 meV. As illustrated in FIG. 9B, polymer chains 210 synthesized from the DBTP 200 are two-dimensionally aggregated. Cohesive energy at that time is calculated. As a result, it turns out that a gain of an aggregate of the polymer chains 210 caused by the $\pi$-$\pi$ interaction is only 9.4 meV.

As has been described, a gain of an aggregate of polymer chains 80, which are synthesized from the DBSP 70, caused by the $\pi$-$\pi$ interaction is larger than a gain of an aggregate of polymer chains 110, which are synthesized from the DBBA 100, caused by the $\pi$-$\pi$ interaction and a gain of an aggregate of polymer chains 210, which are synthesized from the DBTP 200, caused by the $\pi$-$\pi$ interaction. This means that in the stage of synthesis (polymerization) polymer chains 80 synthesized from the DBSP 70 are easily oriented by self-organization compared with polymer chains 110 synthesized from the DBBA 100 and polymer chains 210 synthesized from the DBTP 200.

Polymer chains 80 oriented by self-organization are obtained by using the DBSP 70 as a precursor. As a result, a 9ACGNR having good orientation is realized.

The effect obtained by using the DBSP 70 as a precursor has been described. However, the same effect that is described above is obtained by the use of various compounds represented by formula (2).

In the above description, the DBSP 70 is taken as a concrete example of a compound represented by formula (2). However, still another effect is obtained by, for example, changing a functional group with which an edge of a synthesized graphene nanoribbon is terminated.

For example, a graphene nanoribbon whose edge is terminated with another functional group is obtained by changing the starting material on the route of the synthesis of the precursor illustrated in FIG. 3.

Each of FIG. 10 and FIG. 11 is a view for describing another example of a route of the synthesis of a precursor and a graphene nanoribbon.

In the example of FIG. 10, the compound 20, of the compound 10 and the compound 20 illustrated in FIG. 3 which are starting materials, is replaced with a compound 20a illustrated in FIG. 10, that is to say, with 2-bromo-2', 6'-difluorobiphenyl.

The above compound 20a is used. In accordance with the example of FIG. 3, coupling between a compound 10 (2,6-diiodo-4-nitroaniline) and the compound 20a is performed. After that, an $NH_2$ group is converted to an I atom. Coupling between a compound obtained in this way and a compound 50 is performed. Furthermore, an $NO_2$ group is converted to a Br atom. By doing so, a compound 70a illustrated in FIG. 10 is synthesized. The compound 70a corresponds to the above DBSP 70 part of whose H atoms are replaced by F atoms.

The compound 70a synthesized in this way is used as a precursor. In accordance with the example of FIG. 4, the compound 70a is vacuum-deposited over a catalytic metal substrate to synthesize a polymer chain. Furthermore, aromatic cyclization is performed by high temperature heating. By doing so, a 9ACGNR 90a illustrated in FIG. 10 is synthesized. The 9ACGNR 90a corresponds to the above 9ACGNR 90 H atoms of part of whose edges are replaced by F atoms.

In addition, in the example of FIG. 11, the compound 20, of the compound 10 and the compound 20 illustrated in FIG. 3 which are starting materials, is replaced with a compound 20b illustrated in FIG. 11, that is to say, with 2-bromo-nonafluorobiphenyl.

The above compound 20b is used. In accordance with the example of FIG. 3, coupling between a compound 10 (2,6-diiodo-4-nitroaniline) and the compound 20b is performed. After that, an $NH_2$ group is converted to an I atom. Coupling between a compound obtained in this way and a compound 50 is performed. Furthermore, an $NO_2$ group is converted to a Br atom. By doing so, a compound 70b illustrated in FIG. 11 is synthesized. The compound 70b corresponds to the above DBSP 70 part of whose H atoms are replaced by F atoms.

The compound 70b synthesized in this way is used as a precursor. In accordance with the example of FIG. 4, the compound 70b is vacuum-deposited over a catalytic metal substrate to synthesize a polymer chain. Furthermore, aromatic cyclization is performed by high temperature heating. By doing so, a 9ACGNR 90b illustrated in FIG. 11 is synthesized. The 9ACGNR 90b corresponds to the above 9ACGNR 90 H atoms of whose edges are replaced by F atoms.

As has been described, the 9ACGNR 90a of FIG. 10 whose edges are terminated with F atoms or the 9ACGNR 90b of FIG. 11 whose edges are terminated with F atoms is obtained by changing a starting material at the time of synthesizing a precursor.

The work function of the above 9ACGNR 90 (FIG. 4) whose edges are not terminated with F atoms, that is to say, whose edges are terminated with H atoms is estimated to be 3.59 eV. On the other hand, the work function of the 9ACGNR 90a of FIG. 10 whose edges are terminated with F atoms is estimated to be 3.87 eV. The work function of the 9ACGNR 90b of FIG. 11 whose edges are terminated with F atoms is estimated to be 4.95 eV.

The 9ACGNR 90a (FIG. 10) or the 9ACGNR 90b (FIG. 11) whose work function is higher than that of the above 9ACGNR 90 is obtained by terminating edges in this way with F atoms.

The work function of the 9ACGNR 90a or the 9ACGNR 90b is increased. As a result, n-type operation is realized more easily by connecting as an electrode, for example, metal whose work function is comparatively low. Furthermore, a pn junction is realized by combining the 9ACGNR 90b whose work function is comparatively high with the above 9ACGNR 90 or the 9ACGNR 90a whose work function is comparatively low.

The examples in which the starting material on the route of the synthesis of the precursor illustrated in FIG. 3 is changed have been described. In addition, the following method may be adopted. Treatment for replacing by F atoms determined H atoms of a DBSP 70 synthesized in accordance with the example of FIG. 3 is performed. A compound obtained by this treatment is used as a precursor and a 9ACGNR whose determined edges are terminated with F atoms is synthesized.

Furthermore, the following method may be adopted. A treatment for replacing by F atoms determined H atoms of a 9ACGNR 90 synthesized by the use of a DBSP 70 synthesized in accordance with the example of FIG. 3 is performed. By doing so, a 9ACGNR whose determined edges are terminated with F atoms is synthesized.

Edges of the above 9ACGNRs are terminated with F atoms. By adopting a method for synthesizing a 9ACGNR with a DBSP 70 or its derivative as a precursor or a method for replacing edges of a 9ACGNR synthesized, however, a 9ACGNR whose edges are terminated with a functional group, such as a Cl atom, an alkyl group such as a methyl group ($CH_3$ group), an $NH_2$ group, a hydroxyl group (OH group), or a methoxy group ($OCH_3$), is realized.

In the above description, the above 9ACGNR 90, 9ACGNR 90a, or 9ACGNR 90b is taken as a concrete example of a 9ACGNR represented by formula (11). The DBSP 70 or its derivative is used as a precursor of them. The above 9ACGNR 90, 9ACGNR 90a, or 9ACGNR 90b has width corresponding to nine carbon atoms. By properly selecting a precursor to be used, however, a graphene nanoribbon having any width is synthesized.

A compound used as a precursor of a graphene nanoribbon may have a structure represented by the following formula (12):

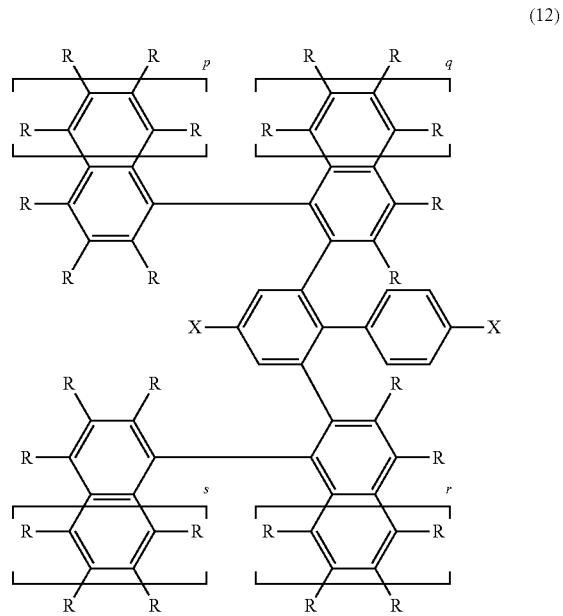

(12)

where X's are independent of each other, are leaving groups, and are preferably Br atoms, Cl atoms, or I atoms, R's are independent of one another and are H atoms, F atoms, Cl atoms, or 1-12C straight-chain, branched-chain, or cyclic alkyl groups, and each of p, q, r, and s is an integer in the range of 0 to 5.

A compound represented by formula (12) is used as a precursor. In accordance with the example of FIG. 4, the compound is vacuum-deposited over a catalytic metal substrate to synthesize a polymer chain. Furthermore, aromatic cyclization is performed by high temperature heating. By doing so, a graphene nanoribbon having a structure represented by the following formula (13) is synthesized:

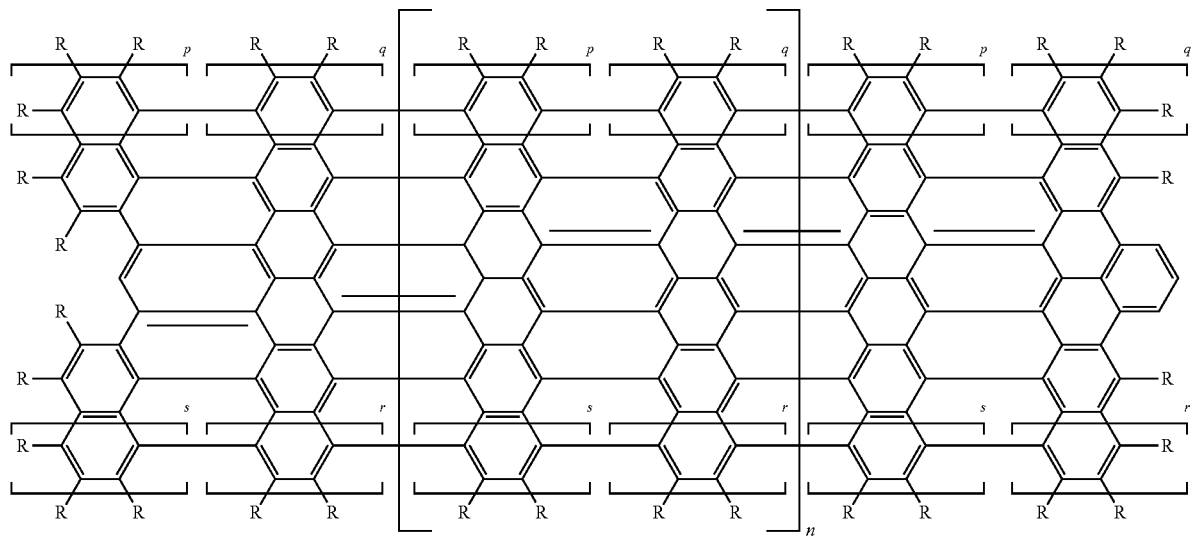

(13)

where R's are independent of one another and are H atoms, F atoms, Cl atoms, or 1-12C straight-chain, branched-chain, or cyclic alkyl groups, n indicates a polymerization degree and is an integer in the range of 0 to 100000, and each of p, q, r, and s is an integer in the range of 0 to 5. A graphene nanoribbon having an armchair edge and having width corresponding to 9 to 29 carbon atoms may be synthesized according to values of p, q, r, and s.

For example, the following method is used.

Figure 12A:
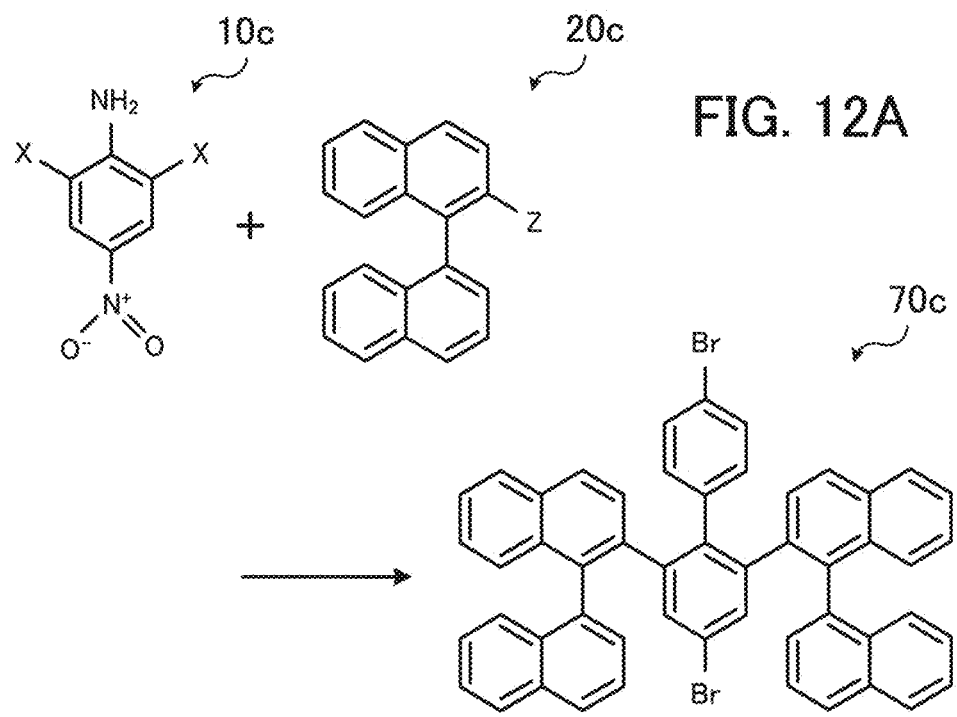
FIGS. 12A and 12B are views for describing an example of a route of the synthesis of a precursor.
Figure 12B:
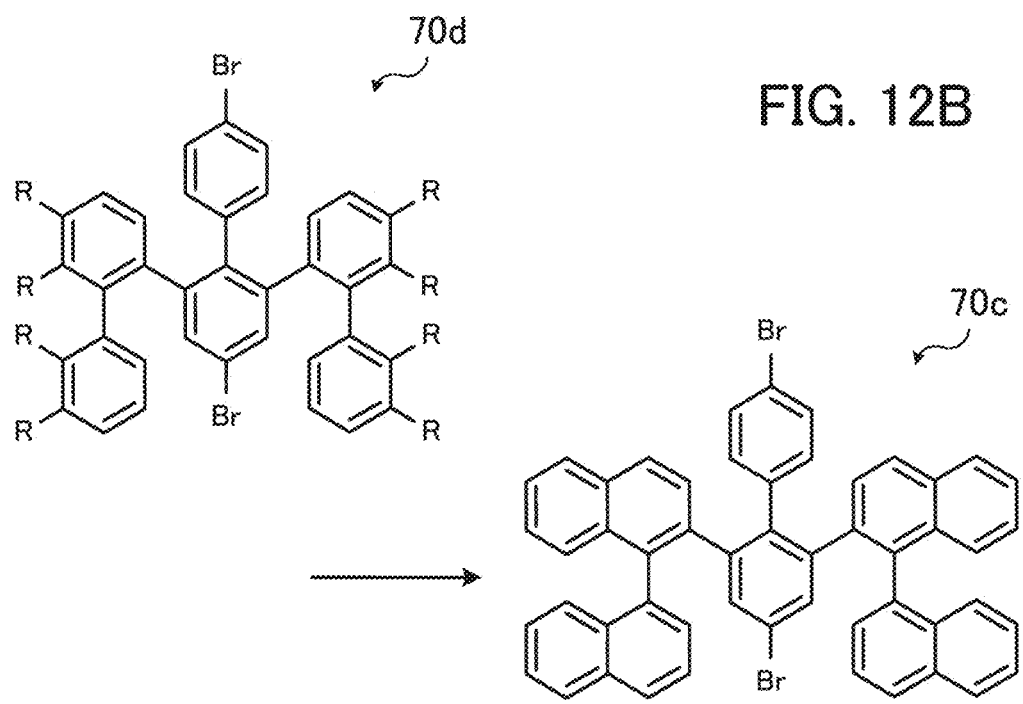

FIGS. 12A and 12B are views for describing an example of a route of the synthesis of a precursor. FIG. 12A illustrates a first example of a route of the synthesis of a precursor. FIG. 12B illustrates a second example of a route of the synthesis of a precursor.

For example, a compound 10c and a compound 20c (binaphthyl derivative) illustrated in FIG. 12A are used as starting materials for the synthesis of a precursor. In FIG. 12, X's are leaving groups, such as I atoms or Br atoms, and Z is a B(OH)$_2$ group, a Br atom, an I atom, or the like. The above compound 10c and compound 20c are used. In accordance with the example of FIG. 3, coupling between the compound 10c and the compound 20c is performed. After that, an NH$_2$ group is converted to a leaving group. Coupling between a compound obtained in this way and a compound 50 is performed. Furthermore, an NO$_2$ group is converted to a leaving group. By doing so, a compound 70c illustrated in FIG. 12A may be synthesized.

Furthermore, as illustrated in FIG. 12B, for example, a compound 70c is synthesized from a compound 70d obtained in accordance with the example of FIG. 3. For example, a starting material in which a functional group containing a determined number of carbons is linked as a side chain R is used. A compound 70d is obtained in accordance with the example of FIG. 3. Aromatic cyclization of its side chain R is performed. Alternatively, a functional group containing a determined number of carbons is introduced as a side chain R into a DBSP 70 obtained in a way illustrated in FIG. 3 to obtain a compound 70d. Aromatic cyclization of its side chain R is performed. A compound 70c illustrated in FIG. 12B may be synthesized in this way.

The above compound 70c (FIG. 12A or FIG. 12B) is used as a precursor and polymerization of a plurality of precursors and aromatic cyclization are performed. By doing so, a graphene nanoribbon having width corresponding to 13 carbon atoms is synthesized.

A precursor, such as the compound 70c, having a symmetrical structure is taken as an example. However, a precursor having an asymmetrical structure may be synthesized for synthesizing a graphene nanoribbon. For example, a precursor having an asymmetrical structure in which a binaphthyl group is linked to one side of a central biphenyl skeleton and in which a biphenyl group is linked to the other side of the central biphenyl skeleton may be synthesized. A graphene nanoribbon having width corresponding to 11 carbon atoms is synthesized by the use of this precursor.

By synthesizing a precursor having a structure represented by formula (12), a graphene nanoribbon having a structure represented by formula (13) and having determined width is synthesized.

From the above viewpoint, a compound having a structure represented by the following formula (14) may be used as a starting material (coupling between the compound 10, the compound 10c, or the like and this starting material is performed) used for synthesizing a precursor having a structure represented by formula (12). In the formula (14), (14)

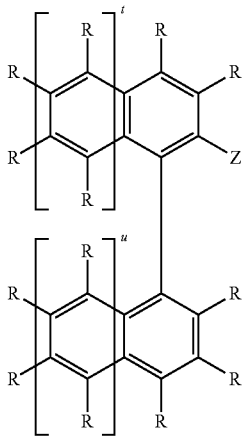

Z is a B(OH)$_2$ group, a Br atom, or an I atom, R's are independent of one another and are H atoms, F atoms, Cl atoms, or 1-12C straight-chain, branched-chain, or cyclic alkyl groups, and each of t and u is an integer in the range of 0 to 5. In this case, p and q in formula (12) correspond to u and t, respectively, in formula (14) which represents a compound used for synthesizing a precursor, and r and s in formula (12) correspond to t and u, respectively, in formula (14) which represents a compound used for synthesizing a precursor.

A use for a compound having a structure represented by formula (12) is not limited to a precursor of a graphene nanoribbon. A compound having a structure represented by formula (12) has other uses.

A second embodiment will now be described.

An example in which a graphene nanoribbon synthesized from the precursors described in the above first embodiment is used in a semiconductor device will now be described as a second example.

Figure 13:
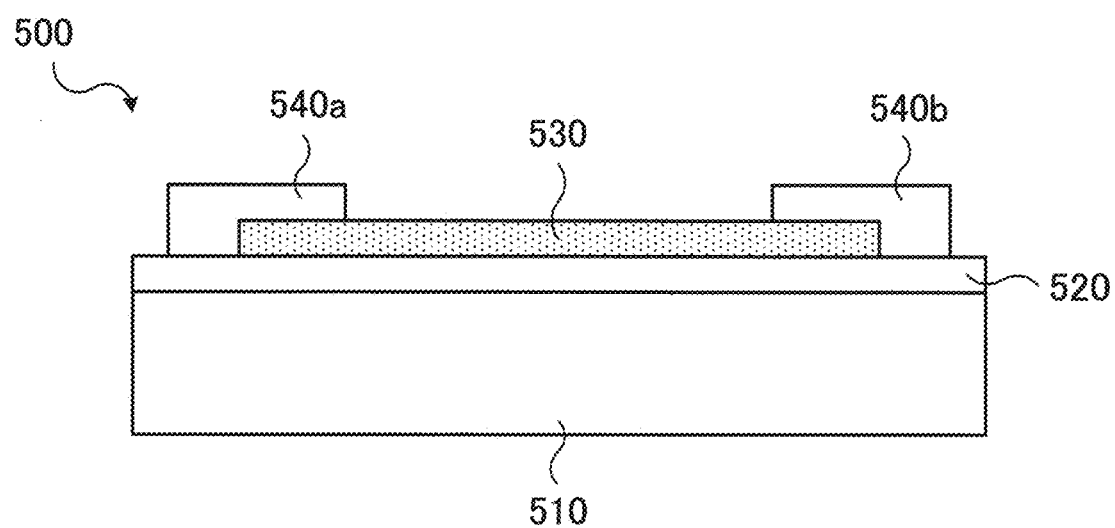
FIG. 13 illustrates a first example of a semiconductor device.

FIG. 13 illustrates a first example of a semiconductor device. FIG. 13 is a schematic sectional view of a semiconductor device.

A semiconductor device 500 illustrated in FIG. 13 is an example of a bottom gate type FET. The semiconductor device 500 includes a gate electrode 510, a gate insulating film 520, a graphene nanoribbon 530, an electrode 540a, and an electrode 540b.

A conductive substrate is used as the gate electrode 510. For example, a semiconductor substrate, such as a silicon (Si) substrate, doped with an impurity element of a determined conduction type is used. The gate insulating film 520 is formed over this gate electrode 510. An insulating material, such as silicon oxide (SiO), is used for forming the gate insulating film 520.

A graphene nanoribbon described in the above first embodiment is used as the graphene nanoribbon 530. That is to say, a graphene nanoribbon obtained by the bottom-up synthesis using the DBSP 70 or the like as a precursor is used as the graphene nanoribbon 530. The graphene nanoribbon 530 is formed by transferring, for example, the graphene nanoribbon obtained by the bottom-up synthesis over the gate insulating film 520 over the gate electrode 510.

The electrode 540a and the electrode 540b are formed over one end portion and the other end portion, respectively, of the graphene nanoribbon 530 formed over the gate insulating film 520. The electrode 540a and the electrode 540b are formed by the use of metal such as titanium (Ti), chromium (Cr), cobalt (Co), nickel (Ni), palladium (Pd), platinum (Pt), aluminum (Al), Cu, Ag, or Au.

With the semiconductor device 500 which is a bottom gate type FET, the graphene nanoribbon 530 is used as a channel. An on state or an off state of the graphene nanoribbon 530 which connects the electrode 540a and the electrode 540b, that is to say, of the channel is controlled by controlling the potential of the gate electrode 510. A high-speed FET is realized by making use of a high carrier mobility of the graphene nanoribbon 530.

The resistance of the graphene nanoribbon 530 changes at the time of adsorbing a molecule. Therefore, the semiconductor device 500 illustrated in FIG. 13 is also used as an FET-type gas sensor by utilizing this property of the graphene nanoribbon 530. With the semiconductor device 500 used as an FET-type gas sensor, a change in the relationship at the time of the graphene nanoribbon 530 adsorbing a gas between a current flowing between the electrode 540a and the electrode 540b and a voltage of the gate electrode 510 is measured. An FET-type gas sensor having high sensitivity is realized by the use of the graphene nanoribbon 530.

Figure 14:
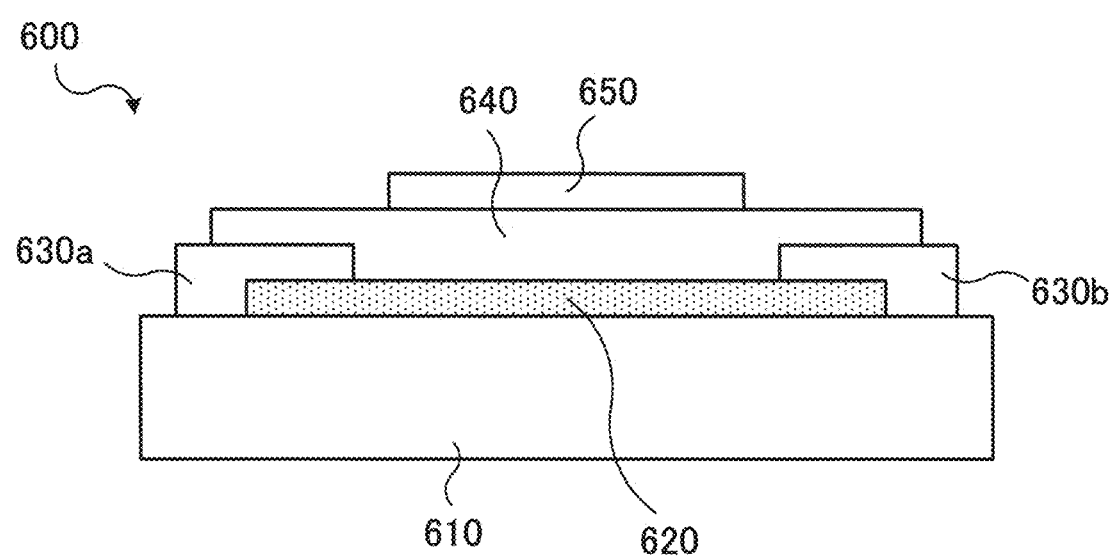
FIG. 14 illustrates a second example of a semiconductor device.

FIG. 14 illustrates a second example of a semiconductor device. FIG. 14 is a schematic sectional view of a semiconductor device.

A semiconductor device 600 illustrated in FIG. 14 is an example of a top gate type FET. The semiconductor device 600 includes a support substrate 610, a graphene nanoribbon 620, an electrode 630a, an electrode 630b, a gate insulating film 640, and a gate electrode 650.

An insulating substrate, such as a sapphire substrate, is used as the support substrate 610. A substrate at least whose surface layer is formed by the use of an inorganic or organic insulating material is used as the support substrate 610. The graphene nanoribbon 620 is formed over the support substrate 610.

A graphene nanoribbon described in the above first embodiment is used as the graphene nanoribbon 620. That is to say, a graphene nanoribbon obtained by the bottom-up synthesis using the DBSP 70 or the like as a precursor is used as the graphene nanoribbon 620. The graphene nanoribbon 620 is formed by transferring, for example, the graphene nanoribbon obtained by the bottom-up synthesis over the support substrate 610.

The electrode 630a and the electrode 630b are formed over one end portion and the other end portion, respectively, of the graphene nanoribbon 620 formed over the support substrate 610. The electrode 630a and the electrode 630b are formed by the use of metal such as Ti, Cr, Co, Ni, Pd, Pt, Al, Cu, Ag, or Au.

The gate electrode 650 is formed over the graphene nanoribbon 620 between the above electrode 630a and electrode 630b with the gate insulating film 640 therebetween. The gate insulating film 640 is formed by the use of an insulating material such as SiO. The gate electrode 650 is formed by the use of polycrystalline silicon or a conductor material such as metal.

With the semiconductor device 600 which is a top gate type FET, the graphene nanoribbon 620 is used as a channel. An on state or an off state of the graphene nanoribbon 620 which connects the electrode 630a and the electrode 630b, that is to say, of the channel is controlled by controlling the potential of the gate electrode 650. A high-speed FET is realized by making use of a high carrier mobility of the graphene nanoribbon 620.

Figure 15:
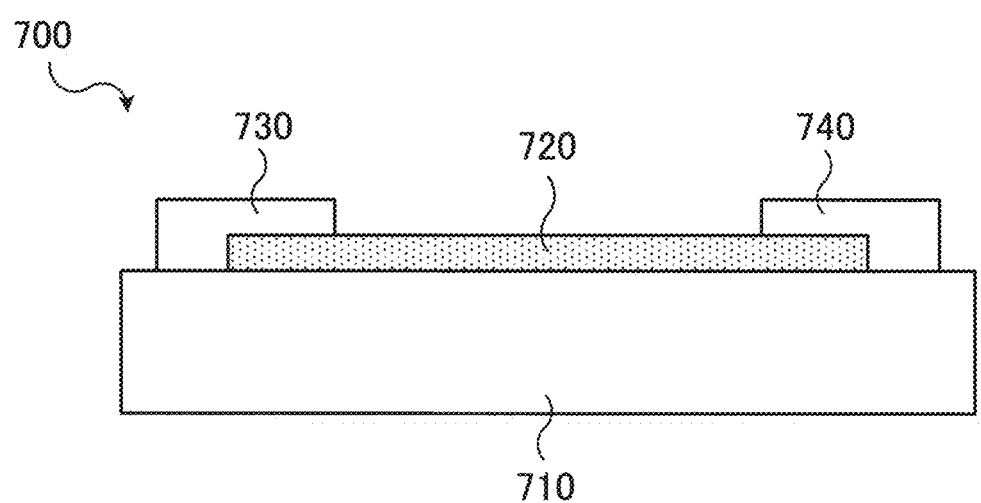
FIG. 15 illustrates a third example of a semiconductor device.

FIG. 15 illustrates a third example of a semiconductor device. FIG. 15 is a schematic sectional view of a semiconductor device.

A semiconductor device 700 illustrated in FIG. 15 is an example of a Schottky barrier diode. The semiconductor device 700 includes a support substrate 710, a graphene nanoribbon 720, an electrode 730, and an electrode 740.

An insulating substrate, such as a sapphire substrate, is used as the support substrate 710. A substrate at least whose surface layer is formed by the use of an inorganic or organic insulating material is used as the support substrate 710. The graphene nanoribbon 720 is formed over the support substrate 710.

A graphene nanoribbon described in the above first embodiment is used as the graphene nanoribbon 720. That is to say, a graphene nanoribbon obtained by the bottom-up synthesis using the DBSP 70 or the like as a precursor is used as the graphene nanoribbon 720. The graphene nanoribbon 720 is formed by transferring, for example, the graphene nanoribbon obtained by the bottom-up synthesis over the support substrate 710.

The electrode 730 and the electrode 740 are formed over one end portion and the other end portion, respectively, of the graphene nanoribbon 720 formed over the support substrate 710. The electrode 730 is formed by the use of metal, such as Cr, which forms a Schottky connection with the graphene nanoribbon 720. The electrode 740 is formed by the use of metal, such as Ti, which forms an ohmic connection with the graphene nanoribbon 720.

With the semiconductor device 700, the graphene nanoribbon 720 is used. A Schottky connection with the electrode 730 is realized on the one end portion side and an ohmic connection with the electrode 740 is realized on the other end portion side. As a result, a Schottky barrier diode having excellent diode characteristics is realized.

The above graphene nanoribbon 530, 620, or 720 may be formed over a material having the function of doping it, for example, what is called a self assembled monolayer (SAM).

A graphene nanoribbon obtained by connecting graphene nanoribbons whose edges are terminated with different functional groups may be used as the above graphene nanoribbon 530, 620, or 720. Furthermore, a graphene nanoribbon obtained by connecting graphene nanoribbons of different widths may be used as the above graphene nanoribbon 530, 620, or 720. In any of these cases, parts which differ in band gap or work function are formed in the graphene nanoribbon 530, 620, or 720. On the basis of the structure of the connected electrodes 540a and 540b, electrodes 630a and 630b, or electrodes 730 and 740, for example, contact resistance or barrier height is controlled by the use of the graphene nanoribbon 530, 620, or 720 including these parts.

Figure 16:
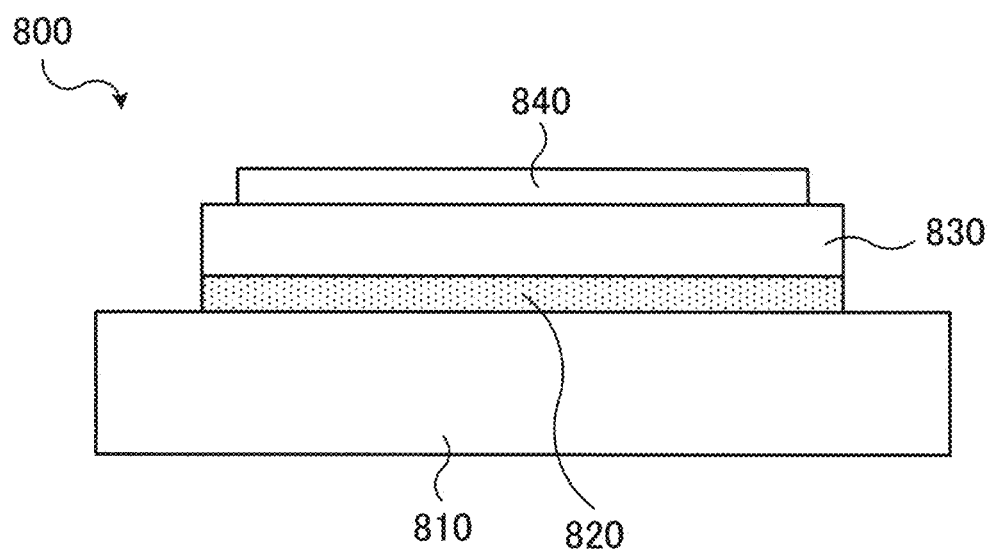
FIG. 16 illustrates a fourth example of a semiconductor device.

Furthermore, FIG. 16 illustrates a fourth example of a semiconductor device. FIG. 16 is a schematic sectional view of a semiconductor device.

A semiconductor device 800 illustrated in FIG. 16 is an example of a laminated solar cell. The semiconductor device 800 includes a lower electrode 810, a graphene nanoribbon 820, a carrier transport layer 830, and an upper electrode 840.

The lower electrode 810 and the upper electrode 840 are formed by the use of a transparent conductor material such as indium tin oxide. Alternatively, one (lower electrode 810, for example) of the lower electrode 810 and the upper electrode 840 is formed by the use of a transparent conductor material and the other (upper electrode 840, for example) of the lower electrode 810 and the upper electrode 840 is formed by the use of an opaque conductor material such as metal.

A quantum dot structure laminate or an organic semiconductor material laminate including a pn junction is used as the carrier transport layer 830 between the lower electrode 810 and the upper electrode 840. For example, the graphene nanoribbon 820 is formed between the lower electrode 810 and the carrier transport layer 830.

A graphene nanoribbon described in the above first embodiment is used as the graphene nanoribbon 820. That is to say, a graphene nanoribbon obtained by the bottom-up synthesis using the DBSP 70 or the like as a precursor is used as the graphene nanoribbon 820.

Light enters the semiconductor device 800 and electrons and holes produced at a pn junction interface in the carrier transport layer 830 reach, for example, the lower electrode 810 and the upper electrode 840 respectively. As a result, electricity is generated. In this case, the graphene nanoribbon 820 disposed between the carrier transport layer 830 and the lower electrode 810 improves the efficiency of extracting electrons to the lower electrode 810 or controls the work function of the lower electrode 810. Furthermore, the graphene nanoribbon 820, together with the lower electrode 810, may be used as part of a lower electrode of a laminated solar cell.

A graphene nanoribbon which improves the efficiency of extracting holes to the upper electrode 840 or which controls the work function of the upper electrode 840 may be disposed between the carrier transport layer 830 and the upper electrode 840. Furthermore, the graphene nanoribbon, together with the upper electrode 840, may be used as part of an upper electrode of a laminated solar cell.

A third embodiment will now be described.

Various electronic devices (also referred to as electronic apparatus) may be equipped with the semiconductor devices 500, 600, 700, 800, and the like according to the above second embodiment. For example, the semiconductor devices 500, 600, 700, 800, and the like according to the above second embodiment may be used in various electronic devices such as computers (personal computers, supercomputers, servers, and the like), smartphones, portable telephones, tablet terminals, sensors, cameras, audio equipment, measuring equipment, inspection equipment, and manufacturing equipment.

Figure 17:
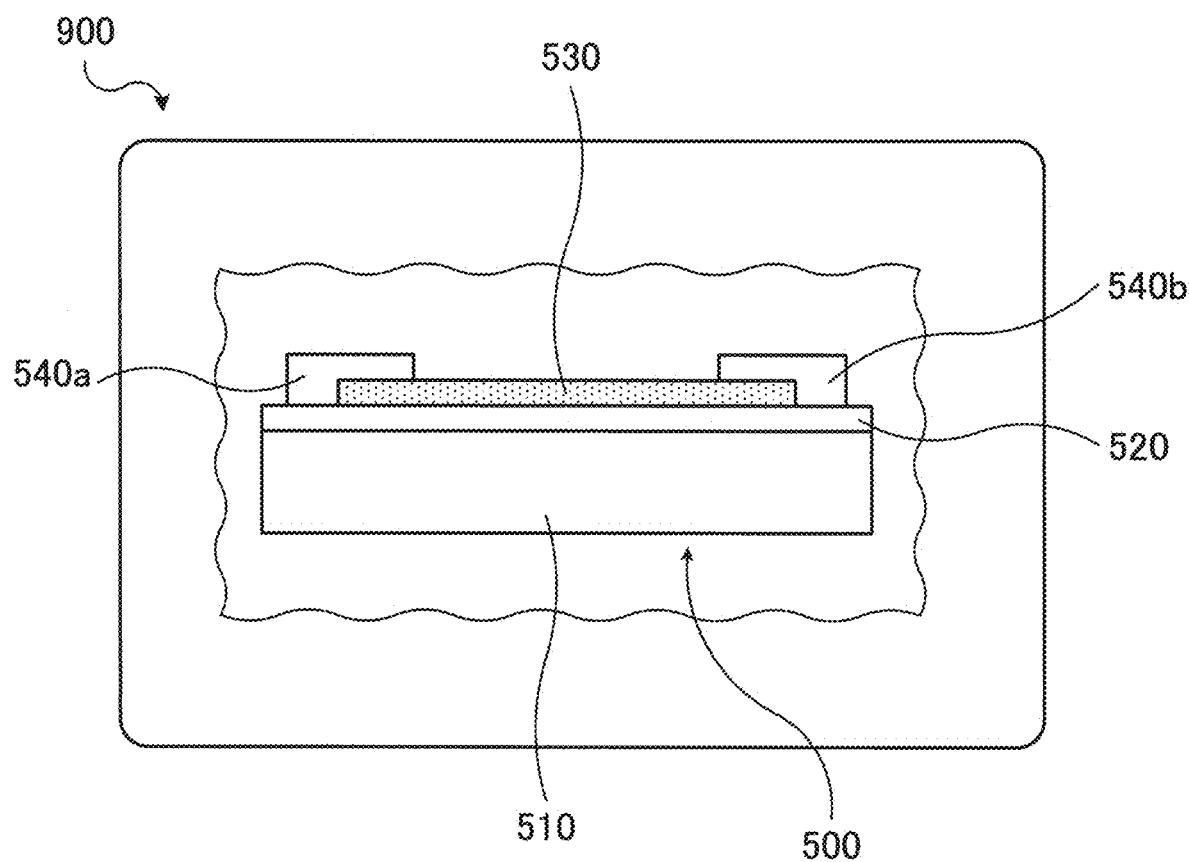
FIG. 17 is a view for describing an electronic device.

FIG. 17 is a view for describing an electronic device. FIG. 17 is a schematic view of an example of an electronic device.

As illustrated in FIG. 17, for example, the semiconductor device 500 illustrated in FIG. 13 is carried by (incorporated in) an electronic device 900. With the semiconductor device 500, as stated above, a high-speed FET is realized by making use of a high carrier mobility of the graphene nanoribbon 530. As a result, a high performance electronic device 900 which carries such a semiconductor device 500 is realized.

The semiconductor device 500 illustrated in FIG. 13 is taken as an example. However, the other semiconductor devices 600, 700, 800, and the like are also carried by various electronic devices.

A graphene nanoribbon excellent in applicability to a semiconductor device is realized.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. A compound represented by the following general formula (1):

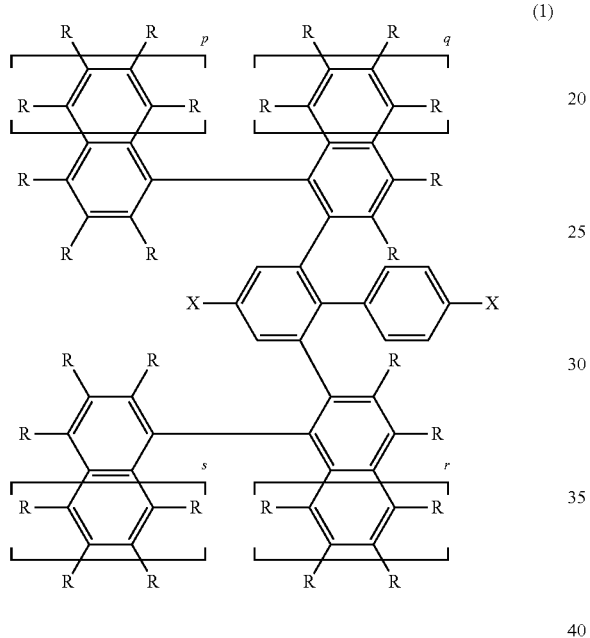

wherein X's are independently selected from bromine atoms, chlorine atoms, or iodine atoms, R's are independently selected from hydrogen atoms, fluorine atoms, chlorine atoms, or 1-12C straight-chain, branched-chain, or cyclic alkyl groups, and each of p, q, r, and s is an integer in the range of 0 to 5.

2. A compound fabrication method comprising:

performing coupling between a first compound comprising an amino group and a nitro group represented by the following general formula (2) and a second compound represented by the following general formula (3), converting the amino group to a leaving group, and synthesizing a third compound; and performing coupling between the third compound and a fourth compound represented by the following general formula (4), converting the nitro group to a leaving group selected from a bromine atom, a chlorine atom, or an iodine atom, and synthesizing a fifth compound represented by the following general formula (5), wherein:

in the general formula (2),

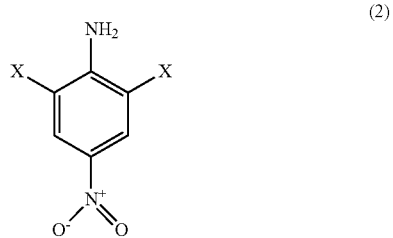

X's are independent of each other and are leaving groups;

in the general formula (3),

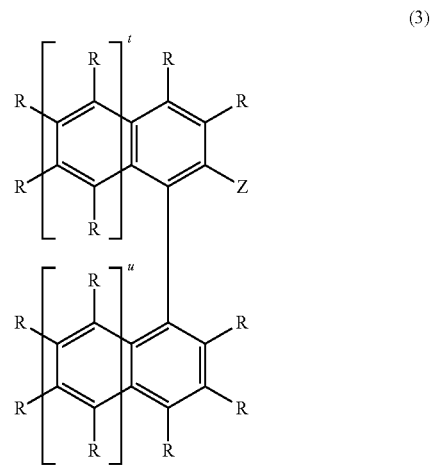

R's are independently selected from hydrogen atoms, fluorine atoms, chlorine atoms, or 1-12C straight-chain, branched-chain, or cyclic alkyl groups, Z is a boronyl group, a bromine atom, or an iodine atom, and each of t and u is an integer in the range of 0 to 5;

in the general formula (4),

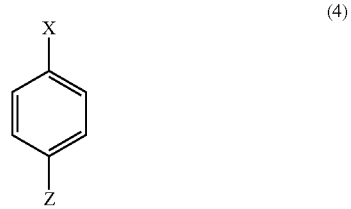

X is a leaving group selected from a bromine atom, a chlorine atom, or an iodine atom, and Z is a boronyl group, a bromine atom, or an iodine atom; and in the general formula (5),

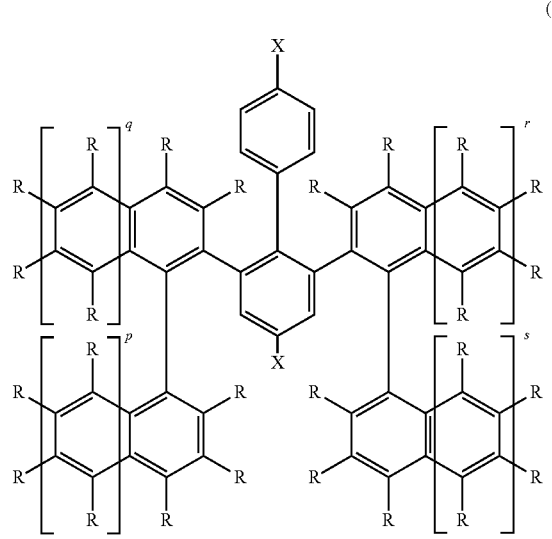

(5)

X's are leaving groups independently selected from bromine atoms, chlorine atoms or iodine atoms, R's are independently selected from hydrogen atoms, fluorine atoms, chlorine atoms, or 1-12C straight-chain, branched-chain, or cyclic alkyl groups, and each of p, q, r, and s is an integer in the range of 0 to 5.

3. The compound fabrication method according to claim 2, further comprising, after the synthesizing of the fifth compound, synthesizing a derivative of the fifth compound.

4. A graphene nanoribbon fabrication method comprising synthesizing a graphene nanoribbon represented by the following general formula (7) by polymerization of a plurality of compounds represented by the following general formula (6) and aromatic cyclization,
wherein:
in the general formula (6),

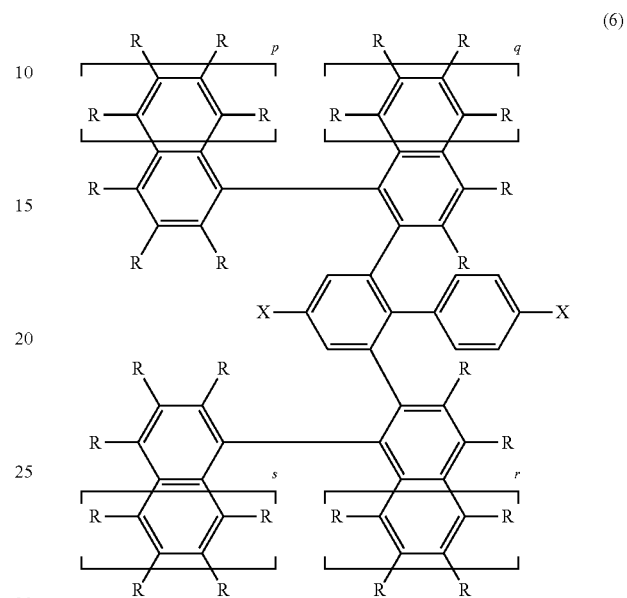

(6)

X's are leaving groups independently selected from bromine atoms, chlorine atoms or iodine atoms, R's are independently selected from hydrogen atoms, fluorine atoms, chlorine atoms, or 1-12C straight-chain, branched-chain, or cyclic alkyl groups, and each of p, q, r, and s is an integer in the range of 0 to 5; and
in the general formula (7),

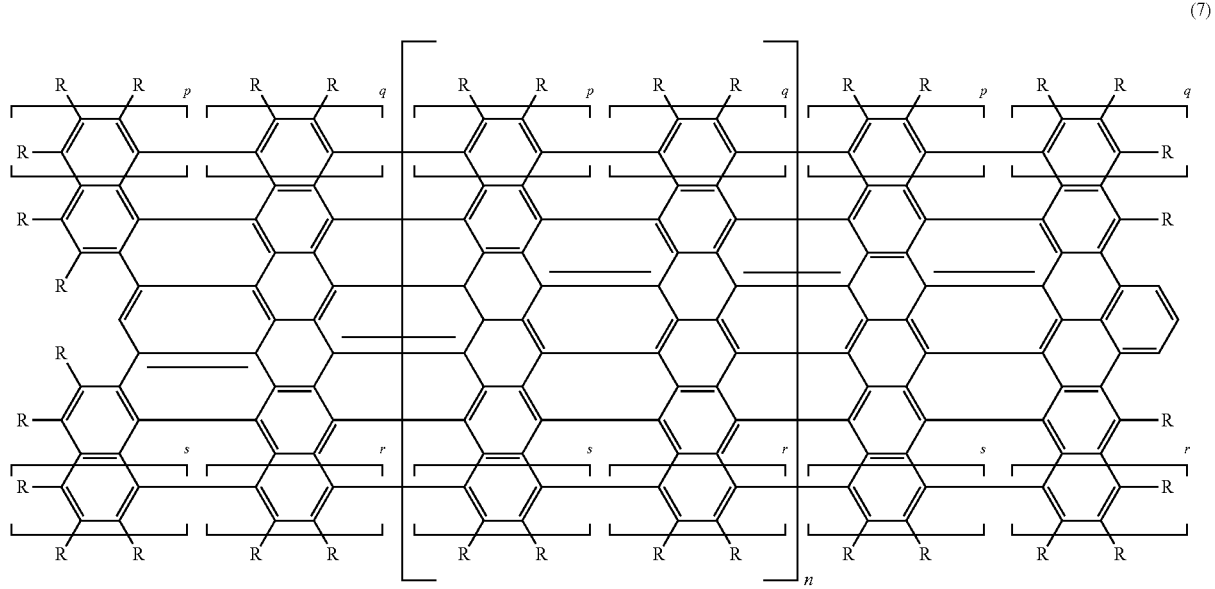

(7)

R's are independently selected from hydrogen atoms, fluorine atoms, chlorine atoms, or 1-12C straight-chain, branched-chain, or cyclic alkyl groups and each of p, q, r, and s is an integer in the range of 0 to 5.

* * * * *